United States Patent [19]

Nakajima et al.

[11] Patent Number: 4,908,379

[45] Date of Patent: Mar. 13, 1990

[54] NITROGEN-CONTAINING HETEROCYCLIC COMPOUNDS AND COMPOSITIONS FOR CONTROLLING AND/OR PREVENTING PESTS AND BLIGHTS (DISEASES)

[75] Inventors: Yasuyuki Nakajima; Takahiro Makabe; Kazunari Nakayama; Tatsuo Numata, all of Funabashi; Kiminori Hirata, Saitama; Masaki Kudo, Saitama; Yoshinori Ochiai, Saitama; Masayoshi Hirose, Tokyo, all of Japan

[73] Assignee: Nissan Chemical Industries Ltd., Tokyo, Japan

[21] Appl. No.: 185,992

[22] Filed: Apr. 25, 1988

[51] Int. Cl.$^4$ .................. C07D 239/56; C07D 239/52; C07D 239/60; A01N 43/54

[52] U.S. Cl. ..................... 514/274; 514/269; 514/258; 244/278; 244/302; 244/313; 244/314; 244/309; 244/319; 244/299; 244/300; 244/301; 244/303; 244/304; 244/305; 244/306

[58] Field of Search ............. 544/299, 300, 301, 302, 544/303, 304, 305, 306, 315, 319, 313, 314, 309; 514/269

[56] References Cited

U.S. PATENT DOCUMENTS

| | | | |
|---|---|---|---|
| 3,853,900 | 12/1974 | Shone | 424/263 |
| 3,855,219 | 12/1974 | Fuchs et al. | 71/93 |
| 3,914,224 | 10/1975 | Jewell | 71/93 |
| 3,985,735 | 10/1976 | Powell | 424/246 |
| 4,540,698 | 9/1985 | Ishikawa et al. | 514/270 |

FOREIGN PATENT DOCUMENTS

| | | |
|---|---|---|
| 0035333 | 9/1981 | European Pat. Off. |
| 0088384 | 9/1983 | European Pat. Off. |
| 0134439 | 3/1985 | European Pat. Off. |
| 018212 | 6/1986 | European Pat. Off. |
| 0193853 | 9/1986 | European Pat. Off. |
| 0199281 | 10/1986 | European Pat. Off. |
| 0232825 | 8/1987 | European Pat. Off. |

OTHER PUBLICATIONS

Prystas et al., Chemical Abstracts, vol. 65, 15969e, (1966).
Mizuno et al., Chemical Abstracts, vol. 82, entry 112039u, (1975).
Fourrey et al., Chemical Abstracts, vol. 86, entry 55382g, (1977).
Rothe et al., Chemical Abstracts, vol. 93, entry 204580u, (1980).
Koshiba et al., Chemical Abstracts, vol. 108, entry 56721b, (1988).

*Primary Examiner*—John M. Ford
*Attorney, Agent, or Firm*—Oliff & Berridge

[57] ABSTRACT

A nitrogen-containing heterocyclic compound of the following formula:

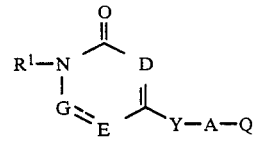

wherein D represents —N= or

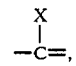

E represents =N—,

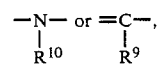

G represents —N=,

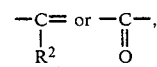

with proviso that when G represents —N= or

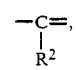

the bond of G and E is double bond; and G represents

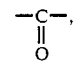

the bond thereof is a single bond, but the case that D represents

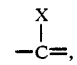

E represents

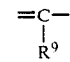

and G represents —N= is omitted ($R^1$, $R^2$, $R^9$, $R^{10}$, X, Y, A and Q are specified in the specification), as well as compositions for controlling and/or preventing pests and blights, said compositions containing one or two or more of said compounds as an active ingredient.

7 Claims, No Drawings

NITROGEN-CONTAINING HETEROCYCLIC COMPOUNDS AND COMPOSITIONS FOR CONTROLLING AND/OR PREVENTING PESTS AND BLIGHTS (DISEASES)

BACKGROUND OF THE INVENTION

1. Field of the Invention

The present invention relates to novel nitrogen-containing heterocyclic compounds, insecticidal, acaricidal, nematicidal compositions and fungicidal compositions for agricultural and horticultural uses, said compositions containing said compounds as an active ingredient.

2. Description of the Prior Art

Hitherto, many insecticidal and acaricidal agents as well as fungicidal agents for agricultural and horticultural uses have been developed, and some of them have been put into practical use. These drugs have contributed to saving works for controlling and preventing pests and blights (or diseases); increasing productivity of agricultural and horticultural crops, domestic cattles and domestic fowls, as well as for improving environments to prevent epidemics.

However, pests and blights (diseases) have become resistant to these drugs and, thus, the effects thereof have not fully been exhibited.

From this viewpoint, there has been a demand for developing novel drugs having superior insecticidal and fungicidal properties.

Compounds which are similar to those of the invention are described in the publications given below. Representatives thereof are illustrated below:

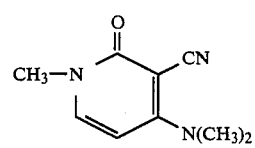
(Compound A)

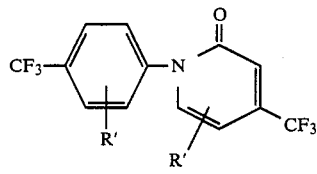
(Compound B)

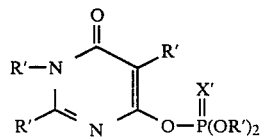
(Compound C)

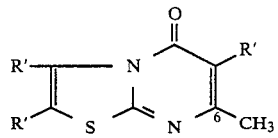
(Compound D)

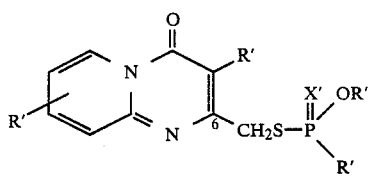
(Compound E)

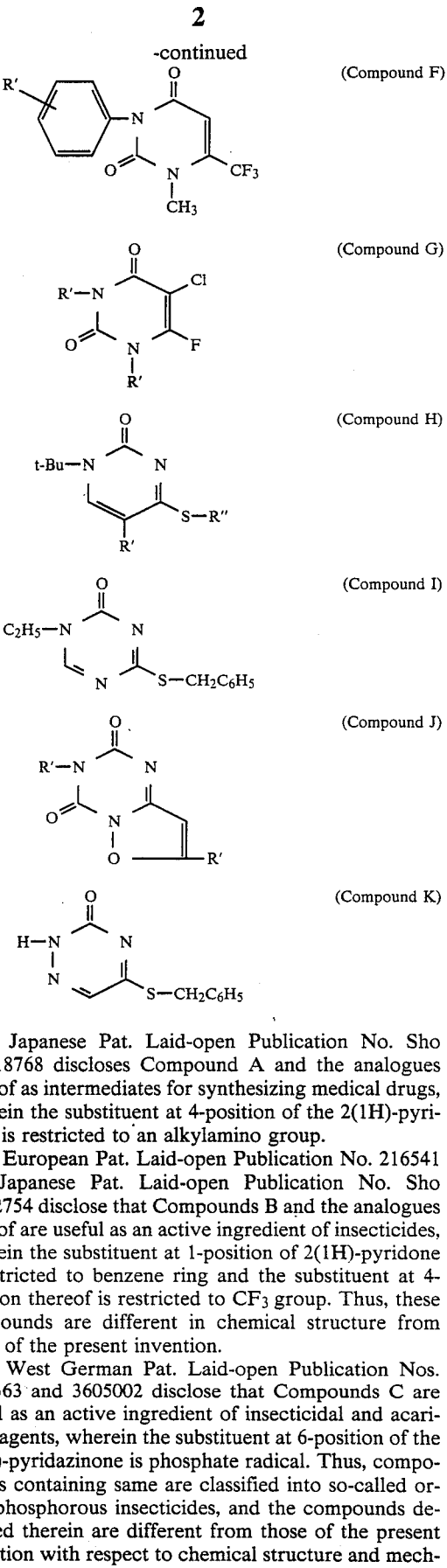

(1) Japanese Pat. Laid-open Publication No. Sho 51-118768 discloses Compound A and the analogues thereof as intermediates for synthesizing medical drugs, wherein the substituent at 4-position of the 2(1H)-pyridone is restricted to an alkylamino group.

(2) European Pat. Laid-open Publication No. 216541 and Japanese Pat. Laid-open Publication No. Sho 61-72754 disclose that Compounds B and the analogues thereof are useful as an active ingredient of insecticides, wherein the substituent at 1-position of 2(1H)-pyridone is restricted to benzene ring and the substituent at 4-position thereof is restricted to $CF_3$ group. Thus, these compounds are different in chemical structure from those of the present invention.

(3) West German Pat. Laid-open Publication Nos. 3439363 and 3605002 disclose that Compounds C are useful as an active ingredient of insecticidal and acaricidal agents, wherein the substituent at 6-position of the 4(3H)-pyridazinone is phosphate radical. Thus, compositions containing same are classified into so-called organophosphorous insecticides, and the compounds described therein are different from those of the present invention with respect to chemical structure and mechanism of insecticidal action.

(4) Japanese Pat. Laid-open Publication No. Sho 54–5995 discloses that Compounds D are useful as an active ingredient of herbicides. Therefore, the compounds described therein are different from those of the invention with respect to uses. Moreover, the substituent at 6-position of thienopyridiminone in the structure of the Compounds D is restricted to an alkyl group.

(5) U.S. Pat. No. 4634690 discloses that Compounds E are useful as an active ingredient of insecticidal, acaricidal and nematicidal compositions. These compounds, however, are different in chemical structure from those of the present invention because the substituent at 6-position of the 4(3H)-pyrimidinone ring of Compound E is restricted to an alkyl group.

(6) Japanese Pat. Laid-open Publication No. Sho 63–41466 discloses that Compounds F are useful as an active ingredient of herbicides. These compounds are different from those of the invention with respect to both their uses and chemical structure.

(7) Japanese Pat. Laid-open Publication No. Sho 61-145167 discloses that Compound G have an antitumor activity. These compounds are different from those of the present invention also in chemical structure.

(8) West German Pat. Laid-open Publication No. 3522805 discloses that Compounds H are useful as an active ingredient of herbicides. Therefore, the compounds described therein are different from those of the present invention in their uses. Moreover, the former compounds are different from the latter in chemical structure because the radical R" in the substituent (SR") at 4-position of the 2(1H)-pyrimidinone of the Compounds H is restricted to an alkyl, an alkenyl or an alkynyl group.

(9) U.S. Pat. No. 3,585,197 discloses that Compounds I are useful as an intermediate for synthesizing a herbicide. These is no description therein as to the biological action of the intermediate. These compounds are different also in chemical structure from those of the invention because the sbustituent at 4-position of the Compounds I is restricted to SCH$_2$C$_6$H$_5$ radical.

(10) U.S. Pat. No. 4,500,345 discloses that Compounds J are useful as an active ingredient of herbicides. The compounds described therein are different from those of the present invention with respect to both their uses and chemical structure.

(11) European Pat. Laid-open Publication No. 35333 discloses that Compounds K are useful as an intermediate for synthesizing a herbicide. There is no description therein as to the biological action of the intermediate itself. The Compounds K are differnet in chemical structure from those of the present invention because the substituent at 5-position of the former compounds is restricted to SCH$_2$C$_6$H$_5$ radical.

SUMMARY OF THE INVENTION

An object of the present invention is to provide novel nitrogen-containing heterocyclic compounds which have activities for controlling and/or preventing pests and blights (diseases).

Another object of the present invention is to provide an insecticidal, acaricidal and nematicidal compositions and fungicidal compositions for agricultural and horticultural uses, said compositions containing the above compounds as an active ingredient.

Other objects of the present invention will become apparent from the description given below.

DETAILED DESCRIPTION OF THE INVENTION

The present invention relates to novel nitrogen-containing heterocyclic compounds and compositions for controlling and/or preventing pests and blights (diseases), said compositions comprising said compounds as an active ingredient.

Namely, the present invention relates to a nitrogen-containing heterocyclic compound of the following formula:

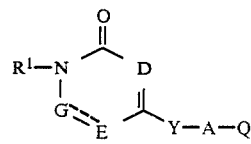

wherein
D represents —N= or

E represents =N—,

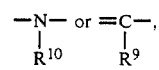

G represents —N=,

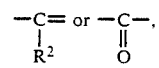

with proviso that when G represents —N= or

the bond of G and E is double bond, and when G represents

the bond thereof is a single bond, but the case that D represents

E represents

and G represents —N= is omitted;
R$^1$ represents an alkyl group having 1 to 10 carbon atoms, an alkenyl group having 2 to 5 carbon atoms, an alkynyl group having 2 to 5 carbon atoms or a cycloalkyl group having 3 to 8 carbon atoms;

$R^2$ represents hydrogen atom, an alkyl group having 1 to 5 carbon atoms, an alkoxy group having 1 to 5 carbon atoms, an alkylthio group having 1 to 5 carbon atoms, an alkylsulfinyl group having 1 to 5 carbon atoms, an alkylsulfonyl group having 1 to 5 carbon atoms, a phenyl unsubstituted or substituted by halogen atom or an alkyl group, and, $R^1$ and $R^2$ together form a ring of the formula:

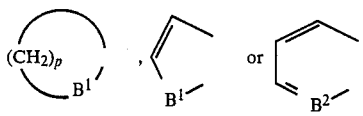

wherein, p represents 2 or 3, $B^1$ represents sulfur atom, oxygen atom or $CH_2$, and $B^2$ represents nitrogen atom or CH:

X represents halogen atom, an alkyl group having 1 to 5 carbon atoms, a phenyl unsubstituted or substituted by halogen atom or an alkyl group, benzyl group, an alkoxy group having 1 to 5 carbon atoms, an alkylthio group having 1 to 5 carbon atoms, nitro group, cyano group, a haloalkyl group having 1 to 5 carbon atoms, or an alkylcarbonyl group having 1 to 5 carbon atoms;

Y represents an oxygen or sulfur atom;

A represents

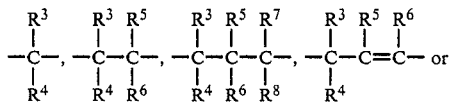

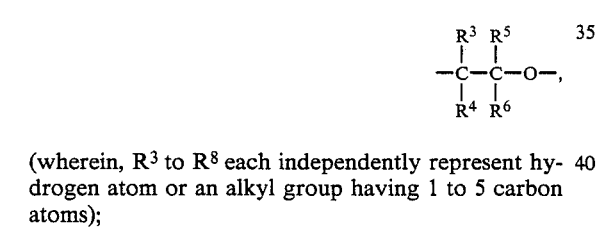

(wherein, $R^3$ to $R^8$ each independently represent hydrogen atom or an alkyl group having 1 to 5 carbon atoms);

Q represents a phenyl gorup having substituents or a pyridine which may have substituents wherein said substituents are selected from the group consisting of halogen atom, an alkyl group having 1 to 10 carbon atoms, a cycloalkyl group having 3 to 6 carbon atoms, an alkyloxy group having 1 to 10 carbon atoms, an alkenyloxy group having 2 to 5 carbon atoms, an alkynyloxy group having 2 to 5 carbon atoms, an alkylthio group having 1 to 5 carbon atoms, a haloalkyl group having 1 to 5 carbon atoms, an alkoxyalkyl group having 1 to 5 carbon atoms, a cyanoalkyl group having 1 to 5 carbon atoms, a haloalkyloxy group having 1 to 5 carbon atoms, a haloalkylthio group having 1 to 5 carbon atoms, an alkoxycarbonyl group having 1 to 5 carbon atoms,

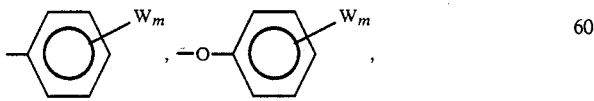

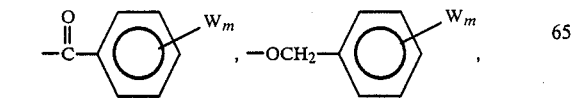

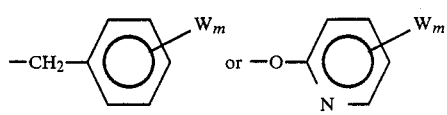

(wherein, W represents halogen atom, an alkyl group having 1 to 5 carbon atoms, an alkoxy group having 1 to 5 carbon atoms, an alkylthio group having 1 to 5 carbon atoms, a haloalkyl group having 1 to 5 carbon atoms, a haloalkoxy group having 1 to 5 carbon atoms or a haloalkylthio group having 1 to 5 carbon atoms; and m represents zero or an integer of from 1 to 4, said W being the same or different when m is an integer of 2 to 4), the number of the substituents being from 1 to 4 and said substituents being the same or different when the number thereof is 2, 3 or 4;

$R^9$ represents hydrogen atom or an alkyl group having 1 to 5 carbon atoms or a halogen atom; and $R^{10}$ represents hydrogen atom or an alkyl group having 1 to 5 carbon atoms, and more specifically the compound represented by any one of the following formulae [I] and [VII]:

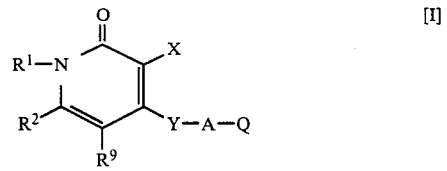

[I]

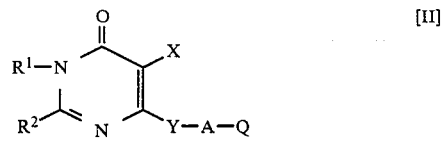

[II]

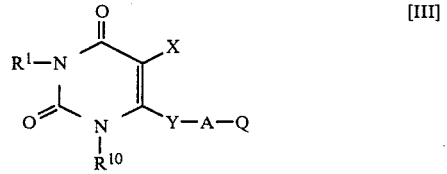

[III]

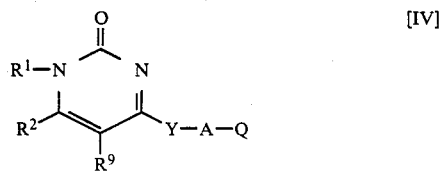

[IV]

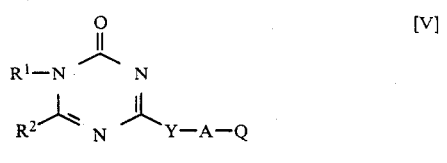

[V]

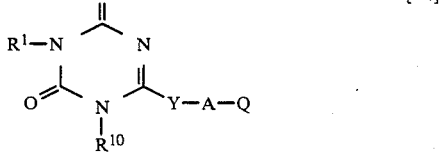

[VI]

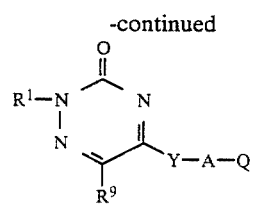
[VII]

wherein $R^1$, $R^2$, $R^9$, $R^{10}$, X, Y, A and Q respectively represent the meaning defined above, as well as compositions for controlling and/or preventing pests and blights (or diseases), said compositions containing one or two or more of said compounds as an active ingredient.

the present inventors have found that the compounds of the present invention represented by one of the general formulae [I] through [VII] have excellent insecticidal, acaricidal, nematicidal actions and fungicidal actions for agricultural and horticultural uses. More specifically, the present inventors have found that the compounds of the invention are very useful for insecticidal, acaricidal and nematicidal compositions and fungicidal compositions for agricultural and horticultural uses; excellent compositions for sanitary and veterinary pest such as ticks, flies and mosquitoes (compositions for prevention of epidemics; and excellent compositions for ectoparasites on animals (e.g., ticks and flies). The present inventors have also found excellent these compounds exhibit excellent insecticidal, nematicidal activities against those pests which are resistant to conventional pesticidal compositions, as well as a long term persistency and/or residual activity to have completed the present invention.

Among the compounds of the present invention, those which have excellent activities for controlling and/or preventing blights (diseases) and pests are described below referring to the compound No. shown in Tables 1 and 2.

Compounds Nos. 54, 68, 72, 73, 74, 75, 118, 119, 122, 123, 125, 139, 140, 141, 144, 145, 146, 147, 149, 150, 154, 155, 156, 159, 161, 196, 218, 219, 220, 221, and 249.

The following compounds exhibit more remarkable effects. Compound Nos. 149, 154, 156 and 161

The compounds of the present invention can be prepared by any one of the following synthetic processes [A] through [C].

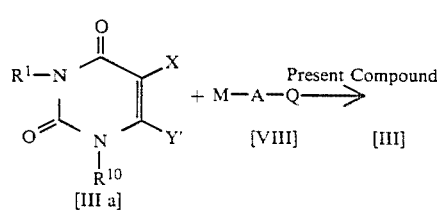
(Process A-3)

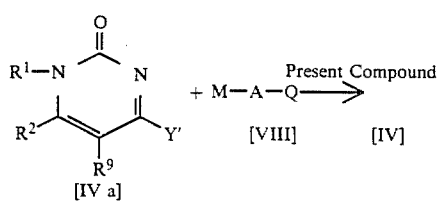
(Process A-4)

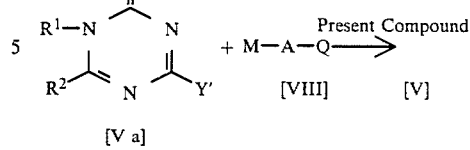
(Process A-5)

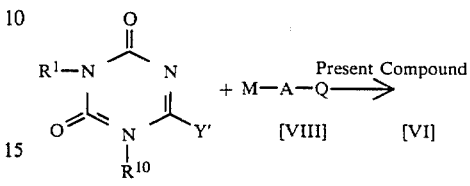
(Process A-6)

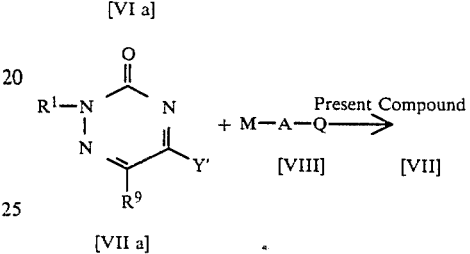
Process A-7)

[Process B]

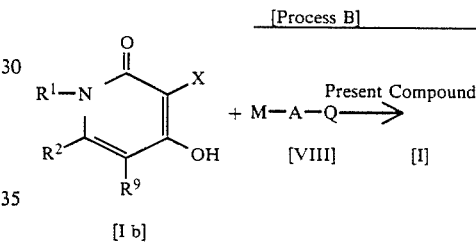
(Process B-1)

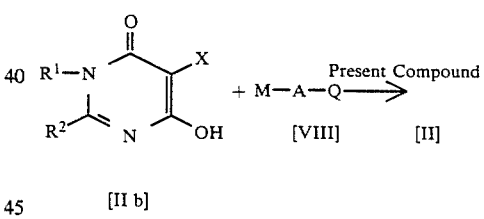
(Process B-2)

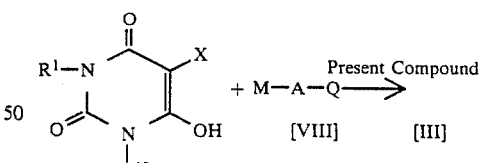
(Process B-3)

[Process C]

(Process C-1)

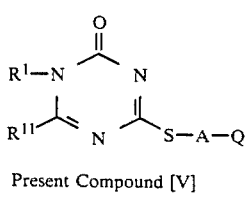

Present Compound [V]

-continued

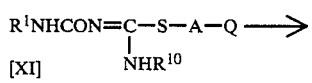

[XI]

(Process C-2)

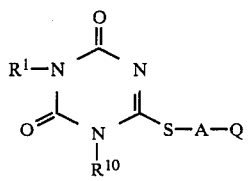

Present Compound [VI]

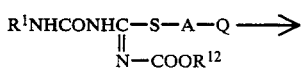

[XII]

(Process C-3)

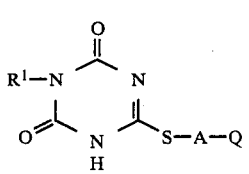

Present Compound [VI]

In the above formulae (in Processes A through C), $R^1$, $R^2$, X, A, Q, $R^9$ and $R^{10}$ each have the same meanings as defined above, Y' represents SH group or halogen atom; M represents halogen atom, methanesulfonate, an arylsulfonate, OH or SH; $R^{11}$ represents hydrogen atom or an alkyl group having 1 to 5 carbon atoms; and $R^{12}$ represents an alkyl group having 1 to 5 carbon atoms.

In the above reaction (in Processes A through B), it is preferable to conduct the reactions in a solvent which does not affect the reaction in the presence of an appropriate base. As such solvents can be used lower alcohols (such as methanol and ethanols, etc.), ketones (such as acetone, methylethylketone, etc.), hydrocarbons (such as benzene, toluene, etc.), ethers (such as isopropylether, tetrahydrofuran, 1,4-dioxane, etc.), amides (such as N,N-dimethylformamine, hexamethylphosphoric triamide, etc.), and halogenated hydrocarbons (such as dichloromethane, dichloroethane). As necessary, it is possible to use mixtures of these solvents or mixtures of the solvent with water.

As the base can be used inorganic bases (such as sodium hydride, sodium hydroxide, potassium hydroxide, sodium carbonate, potassium carbonate, sodium hydrogencarbonate) and organic bases (such as sodium methoxide, sodium ethoxide, triethylamine, pyridine, etc.). As necessary, can be added the reaction system a tetraammonium salt (such as triethylbenzylammonium chloride or the like) as a catalyst. The reaction temperature ranges from $-20°$ C. to the boiling point of the solvent used in the reaction system, and is preferably in the range of from $-5°$ C. to the boiling point of the solvent used therein. Molar ratio of the starting materials can be optionally selected. However, it is advantageous to use the materials in an equimolar ration or near such ratio.

In Process A, a nitrogen-containing heterocyclic compound of the present invention represented by one of the formulae [I] through [VII] can be produced by reacting a compound represented by one of the formulae [Ia] through [VIIa] with a compound of the formula [VIII].

More specifically, in Process A, M in the formula [VIII] represents halogen atom, methanesulfonate or an arylsulfonate, preferably halogen atom and more preferably chloride or bromine atom, when Y' in the formulae [Ia] through [VIIa] is SH group. On the other hand, when Y' in the formulae [Ia] through [VIIa] is halogen atom, M in the formulae [VIII] represents OH or SH group. The solvents preferably used for the reaction include methanol, dioxane, N,N-dimethylformamide, hexamethylphosphoric triamide, toluene, etc. The bases preferably used include inorganic bases, especially sodium carbonate, potassium carbonate, sodium hydroxide, potassium hydroxide, sodium hydride, etc. The reaction temperature is preferably in the range of from $10°$ C. to $80°$ C.

In the case where purification of the compound of the present invention is required, conventional purification technics such as recrystallization, column chromatography, etc. can be used for separation and purification of the compound.

In Process B, a nitrogen-containing heterocyclic compound of the present invention represented by one of the formulae [I] through [III] can be produced by reacting a compound represented by one of the formulae [Ib] through [IIIb] with a compound of the formula [VIII], wherein M represents halogen atom, methanesulfonate or an arylsulfonate.

In Process B, there may be produced C-alkylated substances of the following formula [Ic], [IIc] or [IIIc] as by-products.

In Process B-1

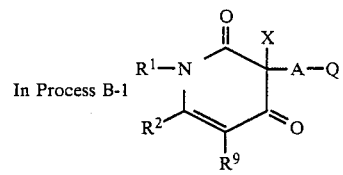

[I c]

In Process B-2

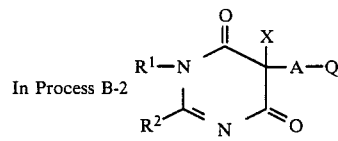

[II c]

In Process B-3

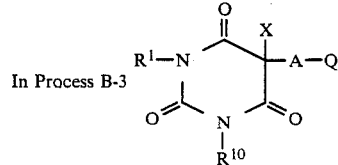

[III c]

In such case, it is necessary to separate these by-products from the compound of the invention to purify the latter compound. Conventional purification technics such as recrystallization, column chromatography, etc. can be used for such separation and purification.

Process C utilizes a cyclization reaction to produce the compounds of the present invention.

In Process C-1, a compound [V] of the present invention can be produced by heating an isothiourea of the formula [IX] and an ortho-ester of the formula [X] in the presence of an organic acid or an inorganic acid.

In Process C-2, a compound [VI] of the present invention can be produced by reacting an isothiourea of the formula [XI] with a carbonylating agent (such as phosgene or the like).

In Process C-3, a compound [VI] of the present invention can be produced by heating an isothiourea of the formula [XII] in the presence of an inorganic base or an organic base.

The compounds according to the present invention are specifically illustrated, for example, by the compounds listed in Tables 1 and 2 below.

Incidentally, it should be understood that the compounds shown in Tables 1 and 2 are only illustrated and that the present invention is not restricted to these compounds.

In the tables below, t represents tertiary, i represents iso, s represents secondary, c represents cyclo, Me represents methyl group, Et represents ethyl group, Pr represents propyl group, Bu represents butyl group, Pen represents pentyl group, Hex represents hexyl group and Ph represents phenyl group.

TABLE 1

In the compounds of the formula:

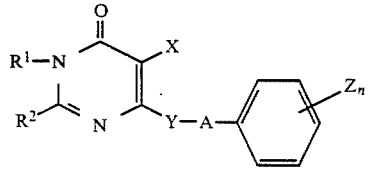

| No. | R¹ | R² | X | Y | A | Zn |
|---|---|---|---|---|---|---|
| 1 | Me | H | Br | S | CH₂ | 4-Cl |
| 2 | Et | H | Br | S | CH₂ | 4-Cl |
| 3 | i-Pr | H | Br | S | CH₂ | 4-Cl |
| 4 | t-Bu | H | Br | S | CH₂ | 4-Cl |
| 5 | Me | H | Br | O | CH₂ | 4-Cl |
| 6 | Me | H | Br | S | CH₂ | 4-Me |
| 7 | Et | H | Br | S | CH₂ | 4-Me |
| 8 | Me | H | Br | S | CH₂ | 4-i-Pr |
| 9 | Et | H | Br | S | CH₂ | 4-i-Pr |
| 10 | Me | H | Br | S | CH₂ | 4-t-Bu |
| 11 | Et | H | Br | S | CH₂ | 4-t-Bu |
| 12 | t-Bu | H | Br | S | CH₂ | 4-t-Bu |
| 13 | Me | H | Br | O | CH₂ | 4-t-Bu |
| 14 | Me | H | Br | S | CH₂ | 4-Hex |
| 15 | Et | H | Br | S | CH₂ | 4-Hex |
| 16 | t-Bu | H | Br | S | CH₂ | 4-c-Hex |
| 17 | Me | H | Br | O | CH₂ | 4-CF₃ |
| 18 | Me | H | Br | S | CH₂ | 4-C₆H₅ |
| 19 | Et | H | Br | S | CH₂ | 4-C₆H₅ |
| 20 | Et | H | Br | S | CH₂ | 4-Q1 |
| 21 | t-Bu | H | Br | O | CH₂ | 4-Q1 |
| 22 | Me | H | Br | O | CH₂ | 4-Q2 |
| 23 | Et | H | Br | O | CH₂ | 4-Q2 |
| 24 | Pr | H | Br | O | CH₂ | 4-Q2 |
| 25 | t-Bu | H | Br | S | CH₂ | 4-Q4 |
| 26 | Me | H | Br | O | CH₂ | 4-Q4 |
| 27 | Et | H | Br | O | CH₂ | 4-Q4 |
| 28 | Pr | H | Br | O | CH₂ | 4-Q4 |
| 29 | Et | H | Br | S | CH₂ | 4-OPr |
| 30 | t-Bu | H | Br | S | CH₂ | 4-OPr |
| 31 | t-Bu | H | Br | S | CHMe | 4-t-Bu |
| 32 | Et | H | Cl | S | CH₂ | 4-t-Bu |
| 33 | t-Bu | H | Cl | O | CH₂ | 4-t-Bu |
| 34 | Et | H | Me | S | CH₂ | 4-t-Bu |
| 35 | t-Bu | H | Me | O | CH₂ | 4-t-Bu |
| 36 | t-Bu | H | Me | S | CH₂ | 4-c-Hex |
| 37 | Me | Me | Br | S | CH₂ | 4-Cl |
| 38 | t-Bu | Me | Br | S | CH₂ | 4-Cl |
| 39 | Me | Me | Br | O | CH₂ | 4-Cl |
| 40 | Me | Me | Br | S | CH₂ | 4-Me |
| 41 | Pr | Me | Br | O | CH₂ | 4-i-Pr |
| 42 | Me | Me | Br | S | CH₂ | 4-t-Bu |
| 43 | t-Bu | Me | Br | S | CH₂ | 4-t-Bu |
| 44 | Me | Me | Br | O | CH₂ | 4-t-Bu |
| 45 | Pr | Me | Br | O | CH₂ | 4-t-Bu |
| 46 | t-Bu | Me | Br | O | CH₂ | 4-t-Bu |
| 47 | Me | Me | Br | S | CH₂ | 4-Hex |
| 48 | t-Bu | Me | Br | S | CH₂ | 4-Hex |
| 49 | t-Bu | Me | Br | S | CH₂ | 4-c-Hex |
| 50 | Me | Me | Br | O | CH₂ | 4-CF₃ |
| 51 | t-Bu | Me | Br | S | CH₂ | 4-C₆H₅ |
| 52 | t-Bu | Me | Br | S | CH₂ | 4-Q1 |
| 53 | Me | Me | Br | O | CH₂ | 4-Q2 |
| 54 | Et | Me | Br | O | CH₂ | 4-Q2 |
| 55 | Pr | Me | Br | O | CH₂ | 4-Q2 |
| 56 | t-Bu | Me | Br | S | CH₂ | 4-Q4 |
| 57 | Me | Me | Br | O | CH₂ | 4-Q4 |
| 58 | Et | Me | Br | O | CH₂ | 4-Q4 |

TABLE 1-continued

In the compounds of the formula:

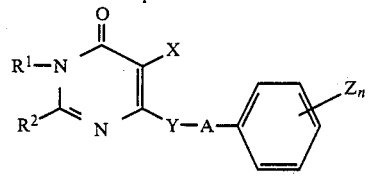

| No. | R¹ | R² | X | Y | A | Zn |
|---|---|---|---|---|---|---|
| 59 | t-Bu | Me | Br | O | $CH_2$ | 4-OPr |
| 60 | t-Bu | Me | Br | S | CHMe | 4-t-Bu |
| 61 | t-Bu | Me | Cl | O | $Ch_2$ | 4-t-Bu |
| 62 | t-Bu | Me | Cl | S | $CH_2$ | 4-c-Hex |
| 63 | t-Bu | Me | Cl | S | $CH_2$ | 4-Q1 |
| 64 | t-Bu | Me | Cl | O | $CH_2$ | 4-Q2 |
| 65 | Et | Me | Me | S | $CH_2$ | 4-t-Bu |
| 66 | t-Bu | Me | Me | S | $CH_2$ | 4-t-Bu |
| 67 | t-Bu | Me | Me | S | $CH_2$ | 4-c-Hex |
| 68 | Et | Me | Me | O | $CH_2$ | 4-Q2 |
| 69 | Et | Me | Me | S | CHMe | 4-t-Bu |
| 70 | Et | Et | Br | S | $CH_2$ | 4-Cl |
| 71 | Et | Et | Cl | S | $CH_2$ | 4-t-Bu |
| 72 | Et | Et | Me | O | $CH_2$ | 4-t-Bu |
| 73 | Et | Et | Me | O | $CH_2$ | 4-c-Hex |
| 74 | Et | Et | Me | O | $CH_2$ | 4-Q1 |
| 75 | Et | Et | Me | O | $CH_2$ | 4-Q2 |
| 76 | Et | i-Pr | Br | S | $CH_2$ | 4-t-Bu |
| 77 | Et | i-Pr | Br | S | $CH_2$ | 4-c-Hex |
| 78 | Me | i-Pr | Br | O | $CH_2$ | 4-Q2 |
| 79 | Et | i-Pr | Br | S | $CH_2$ | 4-OPr |
| 80 | Et | i-Pr | Cl | S | $CH_2$ | 4-t-Bu |
| 81 | Me | t-Bu | Br | S | $CH_2$ | 4-t-Bu |
| 82 | Et | t-Br | Br | S | $CH_2$ | 4-OPr |
| 83 | Me | t-Bu | Cl | S | $CH_2$ | 4-t-Bu |
| 84 | Me | t-Bu | Me | S | $CH_2$ | 4-t-Bu |
| 85 | Me | $C_6H_5$ | Br | O | $CH_2$ | 4-t-Bu |
| 86 | Me | $C_6H_5$ | Br | O | $CH_2$ | 4-Q2 |
| 87 | Me | $C_6H_5$ | Cl | S | $CH_2$ | 4-t-Bu |
| 88 | Et | MeO | Br | S | $CH_2$ | 4-Cl |
| 89 | Et | MeO | Br | S | $CH_2$ | 4-t-Bu |
| 90 | t-Bu | MeO | Br | S | $CH_2$ | 4-t-Bu |
| 91 | Et | MeO | Br | O | $CH_2$ | 4-t-Bu |
| 92 | Et | MeO | Br | S | $CH_2$ | 4-c-Hex |
| 93 | Me | MeO | Br | S | $CH_2$ | 4-Q1 |
| 94 | Et | MeO | Br | O | $CH_2$ | 4-Q2 |
| 95 | Et | MeO | Br | S | $CH_2$ | 4-OPr |
| 96 | t-Bu | MeO | Br | S | $CH_2$ | 4-OPr |
| 97 | Et | MeO | Br | S | CHMe | 4-t-Bu |
| 98 | Et | MeO | Cl | S | $CH_2$ | 4-t-Bu |
| 99 | t-Bu | MeO | Cl | S | $CH_2$ | 4-t-Bu |
| 100 | Et | MeO | Cl | S | $CH_2$ | 4-c-Hex |
| 101 | Et | MeO | Cl | S | $CH_2$ | 4-Q1 |
| 102 | Et | MeO | Cl | S | $CH_2$ | 4-Q2 |
| 103 | t-Bu | MeO | Me | S | $CH_2$ | 4-t-Bu |
| 104 | Et | MeO | Me | O | $CH_2$ | 4-t-Bu |
| 105 | Et | MeO | Me | S | $CH_2$ | 4-Q1 |
| 106 | Et | MeO | Me | S | $CH_2$ | 4-Q2 |
| 107 | t-Bu | MeO | Me | S | $CH_2$ | 4-Q2 |
| 108 | Me | EtO | Br | S | $CH_2$ | 4-t-Bu |
| 109 | Et | EtO | Me | S | $CH_2$ | 4-t-Bu |
| 110 | t-Bu | $CH_2=CHCH_2O$ | Br | S | $CH_2$ | 4-t-Bu |
| 111 | Et | $CH_2=CHCH_2O$ | Me | S | $CH_2$ | 4-Q1 |
| 112 | t-Bu | $CH\equiv CCH_2O$ | Me | O | $CH_2$ | 4-t-Bu |
| 113 | Me | MeS | Br | O | $CH_2$ | 4-Cl |
| 114 | Et | MeS | Br | O | $CH_2$ | 4-Cl |
| 115 | i-Pr | MeS | Br | O | $CH_2$ | 4-Cl |
| 116 | Me | MeS | Br | O | $CH_2$ | 4-i-Pr |
| 117 | Et | MeS | Br | O | $CH_2$ | 4-i-Pr |
| 118 | Me | MeS | Br | O | $CH_2$ | 4-t-Bu |
| 119 | Et | MeS | Br | O | $Ch_2$ | 4-t-Bu |
| 120 | i-Pr | MeS | Br | O | $CH_2$ | 4-t-Bu |
| 121 | t-Bu | MeS | Br | O | $CH_2$ | 4-t-Bu |
| 122 | Me | MeS | Br | O | $CH_2$ | 4-c-Hex |
| 123 | Et | MeS | Br | O | $CH_2$ | 4-c-Hex |
| 124 | i-Pr | MeS | Br | O | $CH_2$ | 4-c-Hex |
| 125 | Me | MeS | Br | O | $CH_2$ | 4-Hex |
| 126 | Me | MeS | Br | O | $CH_2$ | $4-C_6H_5$ |
| 127 | Me | MeS | Br | O | $CH_2$ | 4-OPr |
| 128 | Et | MeS | Br | O | $CH_2$ | 4-Q1 |
| 129 | i-Pr | MeS | Br | O | $CH_2$ | 4-Q1 |

TABLE 1-continued

In the compounds of the formula:

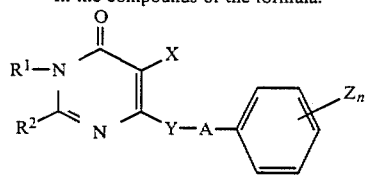

| No. | R¹ | R² | X | Y | A | Zn |
|---|---|---|---|---|---|---|
| 130 | Me | MeS | Br | O | CH₂ | 4-Q2 |
| 131 | Et | MeS | Br | O | CH₂ | 4-Q2 |
| 132 | i-Pr | MeS | Br | O | CH₂ | 4-Q2 |
| 133 | Me | MeS | Br | O | CHMe | 4-t-Bu |
| 134 | Et | MeS | Br | S | CMe₂ | 4-t-Bu |
| 135 | Et | MeS | Cl | O | CH₂ | 4-Q1 |
| 136 | Et | MeS | Me | S | CH₂ | 4-Cl |
| 137 | Me | MeS | Me | O | CH₂ | 4-Cl |
| 138 | Me | MeS | Me | O | CH₂ | 4-i-Pr |
| 139 | Et | MeS | Me | S | CH₂ | 4-t-Bu |
| 140 | Me | MeS | Me | O | CH₂ | 4-t-Bu |
| 141 | Et | MeS | Me | O | CH₂ | 4-t-Bu |
| 142 | Pr | MeS | Me | O | CH₂ | 4-t-Bu |
| 143 | t-Bu | MeS | Me | O | CH₂ | 4-t-Bu |
| 144 | Me | MeS | Me | O | CH₂ | 4-c-Hex |
| 145 | Et | MeS | Me | O | CH₂ | 4-c-Hex |
| 146 | Pr | MeS | Me | O | CH₂ | 4-c-Hex |
| 147 | Et | MeS | Me | O | CH₂ | 4-Bu |
| 148 | Et | MeS | Me | S | CH₂ | 4-CF₃ |
| 149 | Et | MeS | Me | S | CH₂ | 4-OPr |
| 150 | Et | MeS | Me | O | CH₂ | 4-OPr |
| 151 | Me | MeS | Me | O | CH₂ | 3,4-Cl₂ |
| 152 | Pr | MeS | Me | O | CH₂ | 3,4-Cl₂ |
| 153 | Me | MeS | Me | O | CH₂ | 2,4-Cl₂ |
| 154 | Et | MeS | Me | S | CH₂ | 4-Q1 |
| 155 | Me | MeS | Me | O | CH₂ | 4-Q1 |
| 156 | Et | MeS | Me | O | CH₂ | 4-Q1 |
| 157 | Pr | MeS | Me | O | CH₂ | 4-Q1 |
| 158 | t-Bu | MeS | Me | O | CH₂ | 4-Q1 |
| 159 | Et | MeS | Me | S | CH₂ | 4-Q2 |
| 160 | Me | MeS | Me | O | CH₂ | 4-Q2 |
| 161 | Et | MeS | Me | O | CH₂ | 4-Q2 |
| 162 | Pr | MeS | Me | O | CH₂ | 4-Q2 |
| 163 | Me | MeS | Me | O | CH₂ | 4-Q3 |
| 164 | Et | MeS | Me | O | CH₂ | 4-CMe₂CN |
| 165 | t-Bu | MeS | Me | S | CH₂ | 4-OCH₂CF₃ |
| 166 | Et | MeS | Et | O | CH₂ | 4-t-Bu |
| 167 | Et | MeS | Et | O | CH₂ | 4-c-Hex |
| 168 | Et | MeS | Et | O | CH₂ | 4-Q1 |
| 169 | Et | MeS | Et | O | CH₂ | 4-Q2 |
| 170 | Et | MeS | i-Pr | O | CH₂ | 4-Q1 |
| 171 | c-Hex | MeS | Me | S | CH₂ | 4-t-Bu |
| 172 | Et | MeS | MeS(O) | S | CH₂ | 4-t-Bu |
| 173 | Et | MeS | EtS(O) | S | CH₂ | 4-OPr |
| 174 | Et | MeS | MeSO₂ | S | CH₂ | 4-Cl |
| 175 | Me | 4-ClC₆H₄ | Br | O | CH₂ | 4-t-Bu |
| 176 | Me | 4-MeC₆H₄ | Br | O | CH₂ | 4-Q1 |
| 177 | Et | MeS | Me | S | CH₂ | 4-OCH₂CH=CH₂ |
| 178 | Et | MeS | Me | S | CH₂ | 4-OCH₂C≡CH |
| 179 | Et | MeS | Me | S | CH₂CH₂O | 2,6-Me₂-4-OPh |
| 180 | Et | MeS | Me | S | CH₂CH₂O | 2,6-Me₂-4-(OC₆H₄Me-4) |
| 181 | Et | MeS | Me | S | CH₂ | 4-OCHF₂ |
| 182 | Et | MeS | Me | S | CH₂ | 4-COOMe |
| 183 | Me | MeS | Me | S | CH₂ | 4-COOBu-t |
| 184 | Et | MeS | Me | S | CH₂CH₂O | 2,6-Me₂-4-Q5 |
| 185 | Et | MeS | Me | S | CH₂ | 4-Q6 |
| 186 | Et | MeS | Me | O | CH₂ | 4-(C₆H₄-OCHF₂-4) |
| 187 | Et | MeS | Me | O | CH₂ | 4-(C₆H₄-SCHF₂-4) |
| 188 | Et | MeS | Me | S | CH₂ | 4-CO(C₆H₄-SMe-4) |
| 189 | Et | EtS | Br | O | CH₂ | 4-t-Bu |
| 190 | Et | EtS | Br | O | CH₂ | 4-c-Hex |
| 191 | Et | EtS | Br | O | CH₂ | 4-Q2 |
| 192 | Et | EtS | Br | O | CH₂ | 4-F |
| 193 | Et | EtS | Br | O | CH₂ | 3,4-Cl₂ |
| 194 | Et | EtS | Me | O | CH₂ | 4-t-Bu |
| 195 | Et | EtS | Me | O | CH₂ | 4-c-Hex |
| 196 | Et | EtS | Me | O | CH₂ | 4-Q1 |
| 197 | Et | EtS | Me | O | CH₂ | 4-O(CH₂)₄OMe |
| 198 | Et | i-PrS | Me | O | CH₂ | 4-t-Bu |
| 199 | Et | i-PrS | Me | O | CH₂ | 4-c-Hex |
| 200 | Et | i-PrS | Me | O | CH₂ | 4-Q1 |

TABLE 1-continued

In the compounds of the formula:

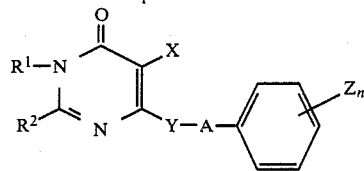

| No. | R$^1$ | R$^2$ | X | Y | A | Zn |
|---|---|---|---|---|---|---|
| 201 | Et | i-PrS | Me | O | CH$_2$ | 4-Q2 |
| 202 | Et | PrS | Br | O | CH$_2$ | 4-t-Bu |
| 203 | Et | PrS | Br | O | CH$_2$ | 4-c-Hex |
| 204 | Et | PrS | Br | O | CH$_2$ | 4-Q1 |
| 205 | Et | PrS | Br | O | CH$_2$ | 4-Q2 |
| 206 | Et | PrS | Br | O | CH$_2$ | 4-F |
| 207 | Et | PrS | Br | O | CH$_2$ | 3,4-Cl$_2$ |
| 208 | t-Bu | PrS | Me | S | CH$_2$ | 4-t-Bu |
| 209 | Et | CH$_2$=CHCH$_2$S | Br | S | CH$_2$ | 4-Q1 |
| 210 | Et | CH$_2$=CHCH$_2$S | Me | S | CH$_2$ | 4-Q1 |
| 211 | Et | CH≡CCH$_2$S | Me | S | CH$_2$ | 4-Q1 |
| 212 | Et | Me$_2$N | Me | S | CH$_2$ | 4-t-Bu |
| 213 | Me | MeS | Br | O | CH$_2$CMe=CH | 4-Br |
| 214 | Me | MeS | Br | O | CH$_2$CMe=CH | 2,4-Cl$_2$ |
| 215 | Me | MeS | Me | O | CH$_2$CH$_2$O | 2,6-Me$_2$—4-Pen |
| 216 | Et | MeS | Me | O | CH$_2$CH$_2$ | 4-Cl |
| 217 | Et | MeS | Br | S | CH$_2$CH$_2$CH$_2$ | 4-OPr |
| 218 | CH$_2$=CHCH$_2$ | MeS | Me | O | CH$_2$ | 4-t-Bu |
| 219 | CH$_2$=CHCH$_2$ | MeS | Me | O | CH$_2$ | 4-c-Hex |
| 220 | CH$_2$=CHCH$_2$ | MeS | Me | O | CH$_2$ | 4-Q1 |
| 221 | CH$_2$=CHCH$_2$ | MeS | Me | O | CH$_2$ | 4-Q2 |
| 222 | CH≡CCH$_2$ | MeS | Me | O | CH$_2$ | 4-Q1 |
| 223 | Et | MeS | Ph | O | CH$_2$ | 4-t-Bu |
| 224 | Et | MeS | Ph | O | CH$_2$ | 4-c-Hex |
| 225 | Et | MeS | Ph | O | CH$_2$ | 4-Q1 |
| 226 | Et | MeS | Ph | O | CH$_2$ | 4-Q2 |
| 227 | Et | MeS | MeO | O | CH$_2$ | 4-t-Bu |
| 228 | Et | MeS | MeO | O | CH$_2$ | 4-Q1 |
| 229 | Et | MeS | MeS | O | CH$_2$ | 4-t-Bu |
| 230 | Et | MeS | NO$_2$ | O | CH$_2$ | 4-Q1 |
| 231 | Et | MeS | CF$_3$ | S | CH$_2$ | 4-t-Bu |
| 232 | Et | MeS | CF$_3$ | S | CH$_2$ | 4-Q1 |
| 233 | Et | Et | Me | O | CH$_2$ | 4-F |
| 234 | Et | MeS | Et | O | CH$_2$ | 3,4-Cl$_2$ |
| 235 | Et | MeS | Et | O | CH$_2$ | 4-i-Pr |
| 236 | Et | EtS | Me | O | CH$_2$ | 3,4-Cl$_2$ |
| 237 | Et. | MeS | Et | O | CH$_2$ | 4-F |
| 238 | Et | EtS | Me | O | CH$_2$ | 4-F |
| 239 | Pr | MeS | Me | O | CH$_2$ | 4-F |
| 240 | Et | Et | Me | O | CH$_2$ | 4-Bu |
| 241 | Et | Et | Me | O | CH$_2$ | 4-i-Pr |
| 242 | CH$_2$=CHCH$_2$ | MeS | Me | O | CH$_2$ | 4-F |
| 243 | CH$_2$=ad,4 CHCH$_2$ | MeS | Me | O | CH$_2$ | 3,4-Cl$_2$ |
| 244 | Et | i-PrS | Me | O | CH$_2$ | 4-F |
| 245 | Et | i-PrS | Me | O | CH$_2$ | 3,4-Cl$_2$ |
| 246 | Et | MeS | Ph | O | CH$_2$ | 4-F |
| 247 | Et | MeS | Ph | O | CH$_2$ | 3,4-Cl$_2$ |
| 248 | Et | MeS | Ph | O | CH$_2$CMe=CH | 2,4-Cl$_2$ |
| 249 | CH$_2$=CHCH$_2$ | MeS | Me | O | CH$_2$ | 4-OPr |
| 250 | Et | EtS | Me | O | CH$_2$ | 4-OPr |
| 251 | Et | MeS | Me | O | CH$_2$CH$_2$O | 2,6-Me$_2$—4-Q7 |
| 252 | Et | MeS | Me | O | CH$_2$CH$_2$O | 2,6-Me$_2$—4-Q8 |
| 253 | Et | MeS | Me | O | CH$_2$CH$_2$O | 2,6-Me$_2$—4-Q9 |
| 254 | Et | MeS | Me | O | CH$_2$CH$_2$O | 2,6-Me$_2$—4-I |
| 255 | Et | MeS | Me | O | CH$_2$CH$_2$O | 2,6-Me$_2$—4-OMe |
| 256 | Et | MeS | Cl | O | CH$_2$ | 4-F |
| 257 | Et | MeS | OMe | O | CH$_2$ | 4-F |
| 258 | Et | MeS | CH$_2$Ph | O | CH$_2$ | 4-Q1 |
| 259 | Et | MeS | CH$_2$Ph | O | CH$_2$ | 4-Q2 |
| 260 | Et | MeS | CH$_2$Ph | O | CH$_2$ | 4-c-Hex |
| 261 | Et | MeS | CH$_2$Ph | O | CH$_2$ | 4-F |
| 262 | Et | MeS | CH$_2$Ph | O | CHMe | 4-t-Bu |
| 263 | Et | MeS | i-Pr | O | CH$_2$ | 4-F |

TABLE 2
No. 301 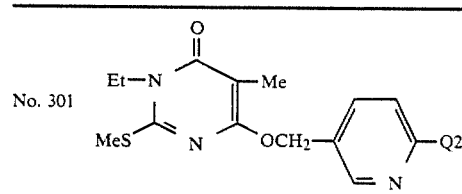
No. 302 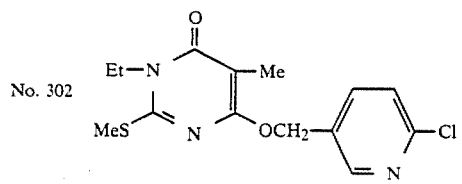
No. 303 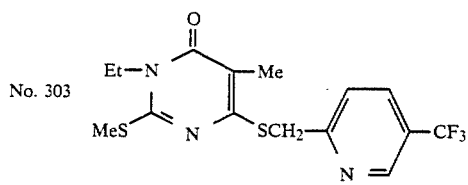
No. 304 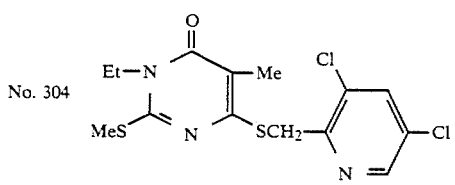
No. 305 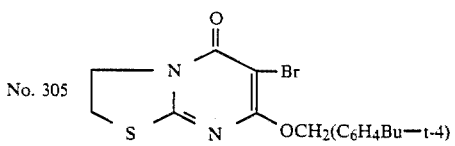
No. 306 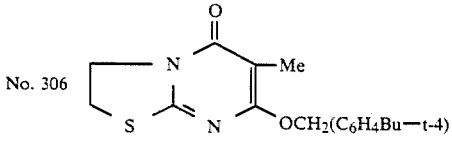
No. 307 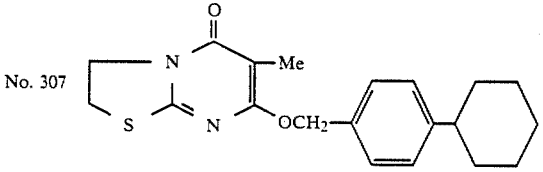
No. 308 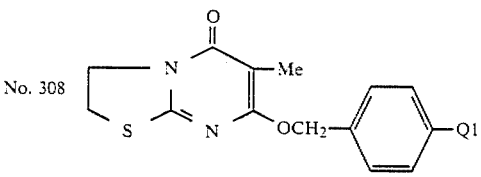
No. 309 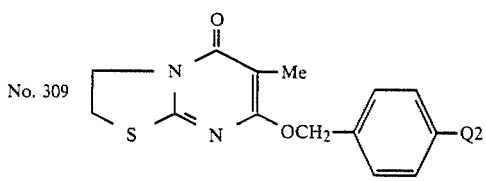
TABLE 2-continued
No. 310 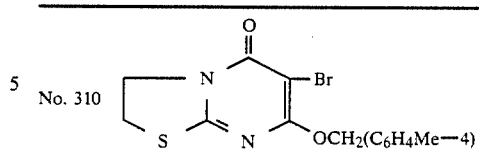
No. 311 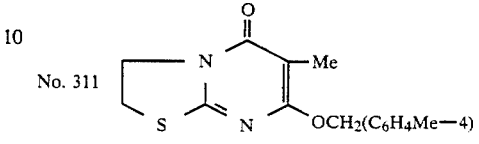
No. 312 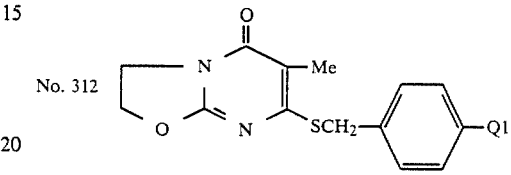
No. 313 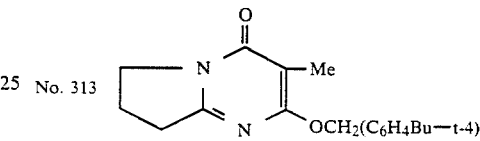
No. 314 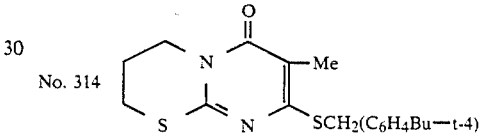
No. 315 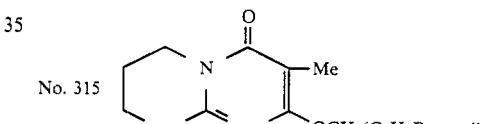
No. 316 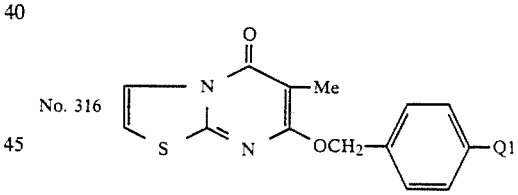
No. 317 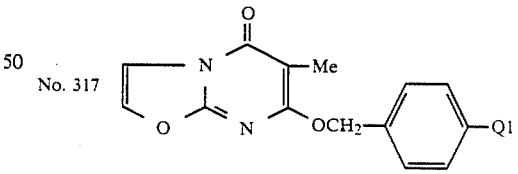
No. 318 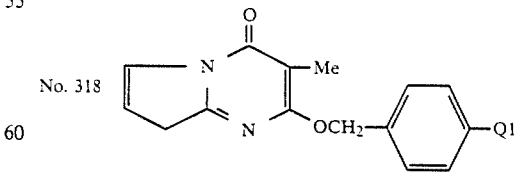
No. 319 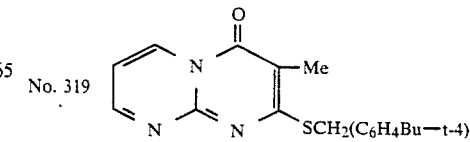

TABLE 2-continued

No. 320: pyrido[1,2-a]pyrimidinone with Me and OCH₂(C₆H₄)Q1 substituents

No. 321: Et—N pyridinone, 3-Cl, 4-OCH₂(C₆H₄Bu-t-4)

No. 322: Et—N pyridinone, 3-Br, 4-SCH₂(C₆H₄-cyclohexyl)

No. 323: Et—N pyridinone, 3-Me, 4-SCH₂(C₆H₄Bu-t-4)

No. 324: t-Bu—N pyridinone, 3-Br, 4-SCH₂(C₆H₄)Q1

No. 325: Et—N pyridinone, 3-Me, 6-Me, 4-SCH₂(C₆H₄)Q2

No. 326: Et—N pyridinone, 3-Br, 6-Me, 5-OCH₂(C₆H₄Bu-t-4)

No. 327: Et—N pyridinone, 3-Cl, 5-Me, 4-SCH₂(C₆H₄OPr-4)

No. 328: Et—N uracil, 5-Cl, 6-SCH₂(C₆H₄Bu-t-4), N-Me

No. 329: Et—N uracil, 5-Cl, 6-SCH₂(C₆H₄Et-4), N-Me

No. 330: Et—N uracil, 5-Me, 6-SCH₂(C₆H₄-cyclohexyl), N-Me

No. 331: t-Bu—N uracil, 5-Cl, 6-SCH₂(C₆H₄OPr-4), N-Me

No. 332: t-Bu—N uracil, 5-Me, 6-OCH₂(C₆H₄)Q1, N-Me

No. 333: t-Bu—N uracil, 5-Br, 6-SCH₂(C₆H₄Cl-4), NH

No. 334: Et—N pyrimidinone, 4-SCH₂(C₆H₄Bu-t-4)

No. 335: t-Bu—N pyrimidinone, 4-SCH₂(C₆H₄Bu-t-4)

No. 336: t-Bu—N pyrimidinone, 4-SCH₂(C₆H₄-cyclohexyl)

No. 337: t-Bu—N pyrimidinone, 4-SCH₂(C₆H₄OPr-4), Me

TABLE 2-continued

No. 338: Et—N(C(=O))—N=CH—N=C(SCH₂(C₆H₄Bu-t-4))

No. 339: t-Bu—N(C(=O))—N=CH—N=C(SCH₂(C₆H₄Bu-t-4))

No. 340: t-Bu—N(C(=O))—N=CH—N=C(SCH₂-C₆H₄-Q1)

No. 341: Et—N(C(=O))—N=C(Me)—N=C(SCH₂-C₆H₄-cyclohexyl)

No. 342: Et—N(C(=O))—N=C(C(=O)NH)—C(SCH₂(C₆H₄Bu-t-4))

No. 343: t-Bu—N(C(=O))—N=C(C(=O)NH)—C(SCH₂(C₆H₄OPr-4))

No. 334: cyclohexyl-N(C(=O))—N=C(C(=O)NH)—C(SCH₂(C₆H₄Bu-t-4))

No. 345: t-Bu—N(C(=O))—N=C(C(=O)N(Me))—C(SCH₂-C₆H₄-cyclohexyl)

No. 346: Et—N(N)—N=CH—C(SCH₂(C₆H₄Bu-t-4))(C(=O))

No. 347: t-Bu—N(N)—N=CH—C(SCH₂(C₆H₄OPr-4))(C(=O))

TABLE 2-continued

No. 348: t-Bu—N(C(=O))—N—N=CH—C(SCH₂-C₆H₄-Q1)

No. 349: Et—N(C(=O))—N—N=C(Me)—C(SCH₂(C₆H₄Et-4))

Incidentally, in case that a compound of the present invention has asymmetric carbon atoms, the optically active (+) isomer and (−) isomer thereof are also included in the present invention.

Moreover, in case that a compound of the present invention has stereoisomers, all the isomers are included in the present invention.

In Tables 1 and 2 above, Q1 through Q9 represents the following groups;

Q1: —O—C₆H₄—CF₃

Q2: —OCH₂—C₆H₄—F

Q3: —CO—C₆H₄—Cl

Q4: —OCH₂—C₆H₄—Cl

Q5: —CH₂—C₆H₄—Me

Q6: —O—(pyridyl)—CF₃

Q7: —CO—C₆H₄(2-CH₃)

Q8: —CO—C₆H₃(2-CH₂, 5-CH₃)

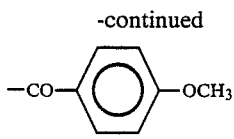 Q9

The compound numbers described in Tables 1 and 2 above are referred to in the following preparation examples, formulation examples and test examples.

The preparation of the present compounds is explained in detail by way of the following working examples which are not to restrict the present invention.

PREPARATION EXAMPLE 1

Synthesis of 5-bromo-6-(4'-t-butylbenzylthio)-3-ethyl-4(3H)-pyrimidinone (Synthesis of Compound No. 11)

In 10 ml of methanol were dissolved 0.48 g of 5-bromo-6-chloro-3-ethyl-4(3H)-pyrimidinone and 0.36 g of 4-t-buthylbenzyl-mercaptan. The resulting solution was incorporated with 0.25 g of sodium carbonate and then stirred for 3 hours at room temperature. The solution was poured into water and then extracted with benzene. The extract was washed with water and dried over anhydrous sodium sulfate. Solvent was distilled off under reduced pressure. The oil thus obtained was purified by means of column chromatography (on silica gel, eluting with benzene) to give 0.73 g of the intended product as a colorless oil.

$^1$H-NMR(CDCl$_3$, δ, TMS) 1.29 (s, 9H), 1.37 (t, 3H, J=7 Hz), 3.95 (q, 2H, J=7 Hz), 4.31 (s, 2H), 7.22 (s, 4H), 7.90 (s, 1H).

PREPARATION EXAMPLE 2

Synthesis of 5-bromo-6-(4'-trifluoromethylbenzyloxy)-3-methyl-4(3H)-pyrimidinone (Synthesis of Compound No. 17)

Sodium hydride (55% in mineral oil) (0.22 g) was suspended in 10 ml of dioxane, and then 0.88 g of 4-trifluoromethylbenzyl alcohol was added thereto. The resulting mixture was stirred for one hour at room temperature, then incorporated with 1.12 g of 5-bromo-6-chloro-3-methyl-4(3H)-pyrimidinone and stirred for 15 hours. The resulting solution was poured into water, and the resulting crystals were filtered off and then recrystallized from a benzene-hexane mixture to give 1.60 g of the intended product.

Melting point (m.p.): 171.9°–172.9° C.

PREPARATION EXAMPLE 3

Synthesis of 5bromo-6-(4'-methylbenzylthio)-2,3-dimethyl-4(3H)-pyrimidinone (Synthesis of Compound No. 40)

In 10 ml of methanol were dissolved 0.59 g of 5-bromo-6-chloro-2,3-dimethyl-4(3H)-pyrimidinone and 0.35 g of 4-methylbenzyl mercaptan and then 0.25 g of sodium carbonate was added thereto. The resulting mixture was stirred for 3 hours at room temperature. The solution thus obtained was poured into water and extracted with benzene. The extract was washed with water and dried over anhydrous sodium sulfate. Solvent was distilled off therefrom under reduced pressure to give an oil. The oil thus obtained was purified by means of column chromatography (on silica gel, eluting with benzene) to give 0.72 g of the intended product.

M.p.: 73.0°–74.0° C.

PREPARATION EXAMPLE 4

Synthesis of 2,5-dimethyl-3-ethyl-6-[4'-(4''-fluoro-benzyloxy)benzyloxy]-4(3H)-pyrimidinone (Synthesis of Compound No. 68)

Sodium hydride (55% in mineral oil) (0.23 g) was suspended in 10 ml of dioxane, and then 1.24 g of 4-(4'-fluorobenzyloxy)benzyl alcohol was added thereto. The resulting mixture was stirred for one hour at room temperature, then incorporated with 1.00 g of 6-chloro-2,5-dimethyl-3-ethyl-4(3H)-pyrimidinone and stirred for 15 hours. The resulting solution was poured into water, and the resulting crystals were filtered off and recrystallized from a benzene-hexane mixture to give 1.83 g of the intended product.

M.p.: 81.0°–82.3° C.

PREPARATION EXAMPLE 5

Synthesis of 2,3-diethyl-5-methyl-6-[4'-(4''-trifluoromethyl-phenoxy)benzyloxy]-4(3H)-pyrimidinone (Synthesis of Compound No. 74)

In 15 ml of N,N-dimethylformamide were dissolved 0.91 g of 2,3-diethyl-6-hydroxy-5-methyl-4(3H)-pyrimidinone and 1.66 g of 4-(4'-trifluoromethylphenoxy)benzyl bromide, and then 0.69 g of potassium carbonate was added thereto. The mixture was stirred for 18 hours at room temperature. The resulting solution was poured into water and extracted with benzene. The extract was washed with water, dried over anhydrous sodium sulfate and freed of solvent by distillation under reduced pressure. The oil thus obtained was purified by means of column chromatography (on silica gel, eluting with benzene) to give 1.35 g of the intended product.

M.p.: 93.8°–95.7° C.

PREPARATION EXAMPLE 6

Synthesis of 5-bromo-6-(4'-chlorobenzyloxy)-2-methylthio-3-i-propyl-4(3H)-pyrimidinone (Synthesis of Compound No. 115)

In 20 ml of N,N-dimethylformamide were dissolved 1.0 g of 5-bromo-6-hydroxy-2-methylthio-3-i-propyl-4(3H)-pyrimidinone and 0.74 g of 4-chlorobenzylbromide, and then 1 g of potassium carbonate was added thereto. The mixture was subjected to a reaction at 80° C. for 3 hours. After allowing to cool in air, the resulting solution was poured into 50 ml of water and then extracted twice with 30 ml of ethyl ether. The ethyl ether layer was washed with water, dried over anhydrous sodium sulfate and freed of solvent by distillation under reduced pressure to give 1.25 g of a crude product. The product was purified by means of column chromatography (on silica gel, eluting with benzene) to give 0.8 g of the intended product as an oil.

n.m.r. (CDCl$_3$, δ, TMS) 1.58 (d, 6H, J=7 Hz), 2.48 (s, 3H), 4.60 (dq, 1H, J=7 Hz), 5.39 (s, 2H), 7.30 (s, 4H).

PREPARATION EXAMPLE 7

Synthesis of 5-bromo-6-(4'-cyclohexylbenzyloxy)-3-ethyl-2-methylthio-4(3H)-pyrimidinone (Synthesis of Compound No. 123)

In 20 ml of N,N-dimethylformamide were dissolved 1 g of 5-bromo-3-ethyl-6-hydroxy-2-methylthio-4(3H)-pyrimidinone and 0.8 g of 4-cyclohexylbenzyl chloride, and then 1 g of anhydrous potassium carbonate was added thereto. The mixture was subjected to a reaction at 80° C. for 3 hours. After allowing to cool in air, the resulting solution was poured into 50 ml of water and extracted twice with 30 ml of ethyl ether. The ethyl ether layer was washed with water, dried over anhydrous sodium sulfate and then freed of solvent by distillation under reduced pressure to give 1.65 g of a crude product.

The product was purified by means of column chromatography (on silica gel, eluting with benzene) to give 0.7 g of the intended product as an oil.

n.m.r. (CDCl$_3$, δ, TMS) 1.31 (t, 3H, J=7 Hz), 1.2–2.1 (m, 10H), 2.53 (s, 3H), 2.3–2.7 (m, 1H), 4.10 (q, 2H, J=7 Hz), 5.41 (s, 2H), 7.05–7.45 (m, 4H).

PREPARATION EXAMPLE 8

Synthesis of 6-(4'-t-butylbenzyloxy)-3,5-dimethyl-2-methylthio-4(3H)-pyrimidinone (Synthesis of Compound No. 140)

In 10 ml of hexamethyl phosphoric triamide were dissolved 1 g of 3,5-dimethyl-6-hydroxy-2-methylthio-4(3H)-pyrimidinone and 1 g of 4-t-butylbenzyl chloride, and thereto was added 0.3 g of sodium hydride (55% in mineral oil). The mixture was stirred for 15 hours at room temperature. The resulting solution was poured into 50 ml of water and then extracted twice with 30 ml of ethyl ether. The ethyl ether layer was dried over anhydrous sodium sulfate and freed of solvent by distillation under reduced pressure to give 1.9 g of a crude product. The product was purified by means of column chromatography (on silica gel, eluting with benzene) and then washed with a mixture of hexane and ethyl ether (10:1) to give 0.8 g of the intended product.

M.p.: 91.0°–96.6° C.

PREPARATION EXAMPLE 9

Synthesis of 3-ethyl-5-methyl-2-methylthio-6-[4'-(4"-trifluoromethylphenoxy)benzyloxy]-4(3H)-pyrimidinone (Synthesis of Compound No. 156)

In 10 ml of hexamethylphosphoric triamide were dissolved 1 g of 6-hydroxy-3-ethyl-5-methyl-2-methylthio-4(3H)-pyrimidinone and 1.66 g of 4-(4'-trifluoromethylphenoxy)benzyl bromide and thereto was added 0.3 g of sodium hydride (55% in mineral oil). The mixture was stirred for 15 hours at room temperature. The resulting solution was poured into 50 ml of water and then extracted twice with 30 ml of ethyl ether. The ethyl ether layer was washed with water, dried over anhydrous sodium sulfate and freed of solvent by distillation under reduced pressure to give 2.1 g of crystals. The crystals were recrystallized from a mixture of hexane and ethyl ether (3:1 ) to give 0.6 g of the intended product.

M.p.: 96.5°–98.0° C.

PREPARATION EXAMPLE 10

Synthesis of 3-ethyl-6-[2'-(4"-fluorobenzyloxy)-5'-pyridylmethyloxy]-5methyl-2-methylthio-4(3H)-pyrimidinone (Synthesis of Compound No. 301)

In 20 ml of N,N-dimethylformamide were dissolved 1 g of 3-ethyl-6-hydroxy-5-methyl-2-methylthio-4(3H)-pyrimidinone and 1.25 g of 2-(4'-fluorobenzyloxy)-5-pyridylmethyl chloride, and thereto was added 1 g of anhydrous potassium carbonate. The mixture was subjected to a reaction at 80° C. for 3 hours.

After allowing to cool in air, the resulting solution was poured into water and then extracted twice with 30 ml of ethyl ether. The ethyl ether layer was washed with water, dried over anhydrous sodium sulfate and freed of solvent by distillation under reduced pressure to give 2.1 g of a crude product.

The product was purified by means of column chromatography (on silica gel, eluting with benzene) and the resulting crystals were washed with a mixture of hexane and ethyl ether (3:1) to give 1.0 g of the intended product.

M.p.: 91.0°–92.2° C.

PREPARATION EXAMPLE 11

Synthesis of 5-bromo-6-(3',4'-dichlorobenzyloxy)-3-ethyl-2-ethylthio-4(3H)-pyrimidinone (Synthesis of Compound No. 193)

In 20 ml of N,N-dimethylformamide were dissolved 1 g of 5-bromo-3-ethyl-2-ethylthio-6-hydroxy-4(3H)-pyrimidinone and 0.7 g of 3,4-dichlorobenzyl chloride, and thereto was added 1 g of potassium carbonate. The mixture was subjected to a reaction at 80° C. for 3 hours.

After allowing to cool in air, the resulting solution was poured into 50 ml of water and then extracted twice with 30 ml of ethyl ether. The ethyl ether layer was washed with water, dried over anhydrous sodium sulfate and freed of solvent by distillation under reduced pressure to give 1.4 g of a crude product.

The product was purified by means of column chromatography (on silica gel, eluting with benzene) to give 0.8 g of the intended product.

M.p.: 93.4°–95.0° C.

PREPARATION EXAMPLE 12

Synthesis of 5-methyl-6-(4'-propyloxybenzylthio)-2-methylthio-3-ethyl-4(3H)-pyrimidinone (Synthesis of Compound No. 149)

Sodium hydride (55% in mineral oil) (0.70 g) was suspended in 20 ml of hexamethyl phosphoric triamide, and then 3.0 g of 4-propyloxybenzyl mercaptan was added thereto. The mixture was stirred for one hour at room temperature and then incorporated with 3.0 g of 6-chloro-5-methyl-2-methylthio-3-ethyl-4(3H)-pyrimidinone. After stirring at room temperature, resulting mixture was heated to 80° C. under stirring for 3 hours. The resulting solution was poured into water and then extracted with benzene. The extract was washed with an aqueous sodium hydroxide solution and then with water, dried over anhydrous sodium sulfate and freed of solvent by distillation udner reduced pressure. The oil thus obtained was purified by means of column chromatography (on silica gel, eluting with chloroform) to give 2.6 g of the intended product.
M.p.: 91.0°–93.0° C.

PREPARATION EXAMPLE 13

Synthesis of 3-cyclohexyl-6-(4'-t-butylbenzylthio)-2,4-(1H, 3H)-triazinedione (Synthesis of Compound No. 344)

A mixture of 1.9 g of N-cyclohexylaminocarbonyl-N'-methoxycarbonyl-S-(4-t-butylbenzyl) isothiourea, 0.3 g of sodium methoxide and 30 ml of methanol was heated under reflux for one hour. After cooling, the resulting crystals were filtered off, washed sufficiently with 0.1N hydrochloric acid and then dried to give 0.9 g of the intended product.

$^1$H-NMR (CDCl$_3$, δ, TMS) 1.0–2.1 (m, 10H), 1.28 (s, 9H), 2.2–2.8 (m, 1H), 4.34 (s, 2H), 6.25 (bs, 1H), 7.27 (s, 4H).

REFERENCE EXAMPLE 1

Synthesis of

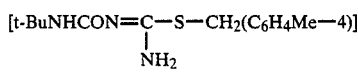

In 30 ml of 50% aqueous solution of methanol was dissolved 9.1 g of S-(4-t-butyl-benzyl) isothiourea.hydrobromide, and thereto was added dropwise 2.6 g of 50% aqueous solution of sodium hydroxide under ice-cooling. After stirring for 15 minutes under ice-cooling, 10 ml of a tetrahydrofuran solution containing 3.0 g of t-butylisocyanate was added dropwise thereto. The mixture was stirred for 3 hours at room temperature. The reaction solution was incorporated with 100 ml of chloroform, washed with water, dried over anhydrous sodium sulfate, and then freed of solvent by distillation under reduced pressure to give 6.9 g of the intended product as a pale yellow solid.

$^1$H-NMR(CDCl$_3$, δ, TMS) 1.27 (s, 9H), 1.31 (s, 9H), 3.65 (bs, 2H), 4.05 (s, 2H), 5.20 (bs, 1H), 7.23 (s, 4H).

According to any one of Preparation Examples 1 through 13, compounds of the present invention were prepared, and the melting points and $^1$H-NMR data of the compounds are shown in Table 3. Compound Nos. therein correspond to those shown in Tables 1 and 2.

TABLE 3

| No. | m.p. (°C.) | $^1$H—NMR data (CDCl$_3$, δ, TMS) |
|---|---|---|
| 1 | 133.1~133.8 | |
| 2 | 109.4~110.7 | |
| 5 | 170.2~173.4 | |
| 6 | 146.4~148.3 | |
| 7 | 127.4~129.0 | |
| 8 | 127.3~128.9 | |
| 9 | 108.7~110.1 | |
| 10 | 183.6~187.4 | |
| 11 | oil | 1.29(s,9H) 1.37(t,3H) 3.95 (q,2H,J=7Hz) 4.31(s,2H) 7.22(s,4H) 7.90(s,1H) |
| 13 | 141.1~147.3 | |
| 14 | 81.5~84.8 | |
| 15 | 124.8~125.1 | |
| 17 | 171.9~172.9 | |
| 18 | 194.1~196.6 | |
| 19 | 154.9~157.9 | |
| 22 | 123.8~125.5 | |
| 23 | 146.2~147.6 | |
| 24 | 149.9~152.0 | |
| 26 | 162.1~164.2 | |
| 27 | 175.9~176.6 | |
| 28 | 171.5~174.6 | |

TABLE 3-continued

| No. | m.p. (°C.) | $^1$H—NMR data (CDCl$_3$, δ, TMS) |
|---|---|---|
| 37 | 106.5~108.3 | |
| 39 | 112.2~114.0 | |
| 40 | 73.0~74.0 | |
| 41 | oil | 0.98(t,3H,J=7Hz) 1.23(d,6H, J=7Hz) 1.63~1.90(m,2H) 2.50(s,3H) 2.76~2.92(m,1H) 3.95(t,2H,J=7Hz) 5.37(s,2H) 7.23(s,4H) |
| 42 | 152.0~153.9 | |
| 44 | 176.2~177.5 | |
| 45 | 100.2~100.8 | |
| 47 | 149.5~150.4 | |
| 50 | 137.5~138.3 | |
| 53 | 151.9~154.1 | |
| 54 | 110.6~111.6 | |
| 55 | 104.3~106.7 | |
| 57 | 98.1~100.3 | |
| 58 | 95.0~98.0 | |
| 68 | 81.0~82.3 | |
| 72 | oil | 1.27(t,3H,J=7Hz) 1.30(s,9H) 1.33(t,3H,J=7Hz) 1.97(s,3H) 2.77(q,2H,J=7Hz) 4.03(q,2H, J=7Hz) 5.37(s,2H) 7.37(s,4H) |
| 73 | oil | 1.17~2.00(m,10H) 1.28(t,3H, J=7Hz) 1.33(t,3H,J=7Hz) 1.95(s,3H) 2.16~2.50(m,1H) 2.70(q,2H,J=7Hz) 4.03(q,2H, J=7Hz) 5.31(s,2H) 7.20(bs,4H) |
| 74 | 93.8~95.7 | |
| 75 | oil | 1.20(t,3H,J=7Hz) 1.27(t,3H, J=7Hz) 1.92(s,3H) 2.64(q, 2H,J=7Hz) 3.93(q,2H,J=7Hz) 4.87(s,2H) 5.25(s,2H) 6.73~ 7.33(m,8H) |
| 78 | 78.0~80.6 | |
| 85 | 85.1~87.3 | |
| 86 | 168.3~169.6 | |
| 113 | 151.1~153.3 | |
| 114 | 119.6~121.1 | |
| 115 | oil | 1.58(d,6H,J=7Hz) 2.48(s,3H) 4.60(dq,1H,J=7Hz) 5.39(s, 2H) 7.30(s,4H) |
| 116 | oil | 1.23(d,6H,J=7Hz) 2.50(s,3H) 2.88(dq,1H,J=7Hz) 3.45(s, 3H) 5.38(s,2H) 7.05~7.40 (m,4H) |
| 117 | oil | 1.24(d,6H,J=7Hz) 1.30(t,3H, J=7Hz) 2.54(s,3H) 2.90(dq, 1H,J=7Hz) 4.10(q,2H,J=7Hz) 5.41(s,2H) 7.05~7.45(m,4H) |
| 118 | 118.5~120.0 | |
| 119 | 106.1~107.0 | |
| 120 | oil | 1.31(s,9H) 1.61(d,6H,J=7Hz) 2.50(s,3H) 4.60(dq,1H, J=7Hz) 5.41(s,2H) 7.32(s,4H) |
| 122 | 142.0~145.0 | |
| 123 | oil | 1.31(t,3H,J=7Hz) 1.20~2.10 (m,10H) 2.53(s,3H) 2.30~ 2.70(m,1H) 4.10(q,2H,J=7Hz) 5.41(s,2H) 7.05~7.45(m,4H) |
| 124 | oil | 1.10~2.10(m,10H) 1.60(d, 6H,J=7Hz) 2.25~2.80(m,1H) 2.49(s,3H) 4.60(dq,1H, J=7Hz) 5.39(s,2H) 7.00~ 7.40(m,4H) |
| 125 | 35.0~42.0 | |
| 126 | 137.3~143.5 | |
| 127 | 101.7~105.0 | |
| 128 | 142.6~143.7 | |
| 129 | 171.9~174.1 | |
| 130 | 159.8~160.2 | |
| 131 | 162.0~164.4 | |
| 132 | 142.0~145.0 | |
| 133 | 160.3~160.9 | |
| 137 | 106.0~110.0 | |
| 138 | oil | 1.25(d,6H,J=7Hz) 1.97(s,3H) 2.50(s,3H) 2.90(dq,1H, J=7Hz) 3.46(s,3H) 5.36(s, 2H) 7.15~7.40(m,4H) |
| 140 | 91.0~96.6 | |
| 141 | 70.0~72.5 | |

TABLE 3-continued

| No. | m.p. (°C.) | ¹H—NMR data (CDCl₃, δ, TMS) |
|---|---|---|
| 142 | oil | 0.98(t,3H,J=7Hz) 1.35(s,9H) 1.52~2.19(m,2H) 1.96(s,3H) 2.51(s,3H) 3.97(t,2H,J=7Hz) 5.38(s,2H) 7.32(s,4H) |
| 144 | oil | 1.10~2.10(m,10H) 1.97(s,3H) 2.25~2.80(m,1H) 2.47(s,3H) 3.40(s,3H) 5.42(s,2H) 7.10~7.40(m,4H) |
| 145 | oil | 1.30(t,3H,J=7Hz) 1.20~2.10(m,10H) 1.97(s,3H) 2.20~2.70(m,1H) 2.49(s,3H) 4.07(q,2H,J=7Hz) 5.37(s,2H) 7.20~7.40(m,4H) |
| 146 | oil | 0.95(t,3H,J=7Hz) 1.20~2.80(m,13H) 1.95(s,3H) 2.50(s,3H) 3.97(t,2H,J=7Hz) 5.35(s,2H) 7.25(s,4H) |
| 147 | oil | 0.92(t,3H,J=7Hz) 1.20~1.80(m,4H) 1.30(t,3H,J=7Hz) 1.96(s,3H) 2.50(s,3H) 2.45~2.70(m,2H) 4.07(q,2H,J=7Hz) 5.37(s,2H) 7.10~7.35(m,4H) |
| 151 | 121.8~122.3 | |
| 152 | 66.5~67.0 | |
| 153 | 160.0~161.1 | |
| 155 | 109.6~110.8 | |
| 156 | 96.5~98.0 | |
| 157 | 88.5~88.9 | |
| 160 | 131.3~132.7 | |
| 161 | 127.0~129.5 | |
| 162 | 109.6~110.0 | |
| 163 | 158.0~164.0 | |
| 301 | 91.0~92.2 | |
| 164 | 111.3~113.2 | |
| 166 | oil | 1.08(t,3H,J=7Hz) 1.30(t,3H,J=7Hz) 1.30(s,9H) 2.50(s,3H) 2.52(q,2H,J=7Hz) 4.05(q,2H,J=7Hz) 5.38(s,2H) 7.31(s,4H) |
| 167 | oil | 1.04(t,3H,J=7Hz) 1.29(t,3H,J=7Hz) 1.10~2.20(m,10H) 2.20~2.80(m,3H) 2.48(s,3H) 4.02(q,2H,J=7Hz) 5.31(s,2H) 7.18(s,4H) |
| 168 | 79.0~80.0 | |
| 169 | 99.5~101.0 | |
| 189 | oil | 1.30(t,3H,J=7Hz) 1.30(s,9H) 1.35(t,3H,J=7Hz) 3.14(q,2H,J=7Hz) 4.09(q,2H,J=7Hz) 5.40(s,2H) 7.32(s,4H) |
| 190 | oil | 1.30(t,3H,J=7Hz) 1.33(t,3H,J=7Hz) 1.20~1.99(m,10H) 2.20~2.80(m,1H) 3.13(q,2H,J=7Hz) 4.07(q,2H,J=7Hz) 5.38(s,2H) 7.20(s,4H) |
| 191 | 123.0~124.0 | |
| 192 | 86.5~87.0 | |
| 193 | 93.4~95.0 | |
| 194 | oil | 1.28(t,3H,J=7Hz) 1.30(s,9H) 1.33(t,3H,J=7Hz) 1.96(s,3H) 3.12(q,2H,J=7Hz) 4.05(q,2H,J=7Hz) 5.32(s,2H) 7.27(s,4H) |
| 195 | oil | 1.28(t,3H,J=7Hz) 1.32(t,3H,J=7Hz) 1.00~2.10(m,10H) 1.95(s,3H) 2.20~2.80(m,1H) 3.10(q,2H,J=7Hz) 4.03(q,2H,J=7Hz) 5.31(s,2H) 7.21(s,4H) |
| 196 | 110.0~111.1 | |
| 197 | oil | 1.30(t,3H,J=7Hz) 1.39(t,3H,J=7Hz), 1.70~2.10(m,4H) 1.95(s,3H) 3.15(q,2H,J=7Hz) 3.31(s,3H) 3.41(t,2H,J=7Hz) 4.00(t,2H,J=7Hz) 4.05(q,2H,J=7Hz) 5.30(s,2H) 6.87(d,2H,J=9Hz) 7.29(d,2H,J=9Hz) |
| 198 | oil | 1.30(t,3H,J=7Hz) 1.35(s,9H) 1.40(d,6H,J=7Hz) 1.98(s,3H) 3.60~4.00(m,1H) 4.07(q,2H,J=7Hz) 5.32(s,2H) 7.31(s,4H) |
| 199 | oil | 1.30(t,3H,J=7Hz) 1.38(d,6H, J=7Hz) 1.15~2.05(m,10H) 1.95(s,3H) 2.20~2.70(m,1H) 3.60~4.20(m,1H) 4.05(q,2H,J=7Hz) 5.31(s,2H) 7.22(s,4H) |
| 200 | 74.0~75.7 | |
| 201 | 94.0~96.0 | |
| 202 | oil | 1.00(t,3H,J=7Hz) 1.31(s,9H) 1.31(t,3H,J=7Hz) 1.55~1.92(m,2H) 3.10(t,2H,J=7Hz) 4.11(q,2H,J=7Hz) 5.40(s,2H) 7.33(s,4H) |
| 203 | oil | 1.00(t,3H,J=7Hz) 1.29(t,3H,J=7Hz) 0.81~2.08(m,12H) 2.16~2.75(m,1H) 3.06(t,2H,J=7Hz) 4.09(q,2H,J=7Hz) 5.48(s,2H) 7.22(s,4H) |
| 204 | 122.0~123.1 | |
| 205 | oil | 1.02(t,3H,J=7Hz) 1.3(t,3H,J=7Hz) 1.60~1.84(m,2H) 3.11(t,2H,J=7Hz) 4.10(q,2H,J=7Hz) 5.00(s,2H) 5.36(s,2H) 6.85~7.51(m,8H) |
| 206 | 96.7~97.8 | |
| 207 | 101.6~102.5 | |
| 213 | 152.7~154.3 | |
| 214 | 160.0~164.1 | |
| 215 | 82.0~85.0 | |
| 218 | oil | 1.31(s,9H) 1.96(s,3H) 2.51(s,3H) 4.62(d,2H,J=5Hz) 5.00~6.10(m,3H) 5.37(s,2H) 7.33(s,4H) |
| 219 | oil | 1.09~2.80(m,11H) 1.96(s,3H) 2.50(s,3H) 4.63(d,2H,J=5Hz) 5.00~6.30(m,3H) 5.36(s,2H) 7.22(s,4H) |
| 220 | 91.0~92.0 | |
| 221 | 98.0~99.1 | |
| 223 | oil | 1.30(s,9H) 1.32(t,3H,J=7Hz) 2.53(s,3H) 4.10(q,2H,J=7Hz) 5.38(s,2H) 7.01~7.69(m,9H) |
| 224 | oil | 1.10~2.22(m,10H) 1.35(t,3H,J=7Hz) 2.30~2.80(m,1H) 2.55(s,3H) 4.12(q,2H,J=7Hz) 5.38(s,2H) 7.18~7.70(m,9H) |
| 225 | 107.2~109.0 | |
| 226 | 125.0~128.0 | |
| 135 | 105.1~106.2 | |
| 136 | 103.0~105.0 | |
| 139 | oil | 1.29(s,9H), 1.31(t,3H), 2.00(s,3H), 2.52(s,3H), 4.08(q,2H), 4.40(s,2H), 7.28(bs,4H) |
| 148 | 122.0~124.0 | |
| 149 | 91.0~93.0 | |
| 150 | 47.0~48.0 | |
| 154 | 109.0~111.0 | |
| 159 | 154.0~158.0 | |
| 170 | oil | 1.25(d,6H), 1.30(t,3H), 2.50(s,3H), 3.30(dq,1H), 4.03(q,2H) 5.32(s,2H), 6.9~7.6(m,8H) |
| 228 | 79.6~81.5 | |
| 305 | 122.0~124.0 | |
| 306 | 141.7~143.6 | |
| 307 | 95.4~113.3 | |
| 308 | 101.9~103.1 | |
| 309 | 133.8~134.9 | |
| 233 | 192.1~193.4 | |
| 234 | oil | 1.08(t,3H), 1.30(t,3H), 2.50(s,3H), 2.45(q,2H), 4.05(q,2H), 5.33(s,2H), 7.1~7.5(m,3H) |
| 235 | oil | 1.08(t,3H), 1.25(d,6H), 1.30(t,3H), 2.45(q,2H), 2.49(s,3H), 2.85(dq,1H), 4.05(q,2H), 5.35(s,2H), 8.22(bs,4H) |
| 236 | 130.0~130.2 | |
| 237 | 80.0~81.3 | |
| 238 | 79.5~80.4 | |
| 239 | oil | 0.98(t,3H), 1.5~1.9(m,2H), 1.95(s,3H), 2.48(s,3H), 3.95(t,3H), 5.32(s,2H), 6.9~7.4 (m,4H) |
| 240 | oil | 0.9~1.6(m,13H), 1.96(s,3H), 2.5~2.9(m,4H), 4.05(q,2H), |

TABLE 3-continued

| No. | m.p. (°C.) | ¹H—NMR data (CDCl₃, δ, TMS) |
|---|---|---|
| 241 | oil | 5.31(s,2H), 6.9~7.4(m,4H) 1.0~1.4(m,12H), 1.95(s,3H), 2.5~3.2(m,3H), 4.01(q,2H), 5.32(s,2H), 7.0~7.3(m,4H) |
| 242 | oil | 1.92(s,3H), 2.49(s,3H), 4.60 (d,2H), 5.0~6.1(m,3H), 5.30 (s,2H), 6.8~7.4(m,4H) |
| 243 | 93.4~94.5 | |
| 244 | 84.6~85.8 | |
| 245 | 120.0~121.0 | |
| 246 | 111.0~113.0 | |
| 247 | 119.6~122.4 | |
| 248 | 124.7~125.8 | |
| 249 | 60.6~62.5 | |
| 250 | 69.2~70.5 | |
| 251 | 129.4~130.2 | |
| 252 | 98.0~100.0 | |
| 253 | 131.0~132.0 | |
| 254 | 93.0~94.5 | |
| 255 | 106.9~107.8 | |
| 256 | 131.6~132.7 | |
| 257 | oil | 1.30(t,3H), 2.49(s,3H), 3.79 (s,3H), 4.50(q,2H), 5.40(s,2H), 6.9~7.4(m,4H) |
| 258 | oil | 1.30(t,3H), 2.30(s,3H), 3.62 (s,2H), 3.85(q,2H), 5.13(s,2H), 6.7~7.4(m,13H) |
| 259 | oil | 1.28(t,3H), 2.43(s,3H), 3.72 (s,2H), 4.02(q,2H), 4.96(s,2H), 5.30(s,2H), 6.8~7.4(m,13H) |
| 260 | oil | 1.27(t,3H), 1.3~2.0(m,11H), 2.42(s,3H), 3.78(s,2H), 4.03(q,2H), 5.31(s,2H), 8.0~8.3(m,9H) |
| 261 | oil | 1.26(t,3H), 2.40(s,3H), 3.78(s,3H), 4.00(q,2H), 5.28(s,2H), 6.8~7.3(m,9H) |
| 262 | oil | 1.25(t,3H), 1.29(s,9H), 1.59(d,3H), 2.36(s,3H), 3.80(s,2H), 4.00(q,2H), 6.05(q,1H), 7.1~7.4(m,9H) |
| 263 | oil | 1.23(d,3H), 1.29(t,3H), 2.48(s,3H), 3.35(dp,1H), 4.03(q,2H), 5.33(s,2H), 6.9~7.5(m,4H) |
| 310 | 161.0~163.0 | |
| 311 | 131.0~131.7 | |
| 344 | white crystal | 1.0~2.1(m,10H), 1.28(s,9H), 2.2~2.8(m,1H), 4.34(s,2H), 6.25(bs,1H), 7.27(s,4H), |

When the compounds of the present invention are used for insecticidal, acaricidal, nematicidal and/or fungicidal agents for agricultural and horticultural uses, sanitary and veterinary insect pest-controlling agents and for expellents of ectoparasites on animals, they are generally mixed with suitable carriers such as solid carriers, e.g., clay, talc, bentonite or diatomaceous earth, or liquid carriers, e.g., water, alcohols (methanol, ethanol, etc.), aromatic hydrocarbons (benzene, toluene, xylene, etc.), chlorinated hydrocarbons, ethers, ketones, esters (ethyl acetate, etc.), acid amides (dimethyl formamide etc.), or the like. If desired, these mixtures may be incorporated with an emulsifier, dispersing agent, suspending agent, penetrating agent, spreader, and/or stabilizing agent to form liquid preparations, emulsifiable concentrates, wettable powders, dusts, granules, flowables, poison baits, solutions, atomizing agents, smoking agents or the like for practical uses. The above-mentioned solution means a preparation wherein an active ingredient is added to a paraffin oil, corn oil or rapeseed oil for the use of controlling ectoparasites on animals, especially by painting and/or spraying. If necessary, the resulting mixtures may be incorporated with other herbicides, various insecticides, fungicides, plant-growth regulating agents, synergists, sanitary and veterinary insect pest-controlling agents and/or animals drugs during preparation or application thereof. The kinds of the compounds to be added are described, for example, in Farm Chemicals Handbook, 73 edition (1987).

The amount of the compounds of the invention to be used as an active ingredient is generally in the range of 0.005 to 5 Kg per hectare (diluted with water to give a diluted solution containing an active ingredient in a concentration of 2 to 50,000 ppm) although it varies depending upon the place and the season where the compounds are applied, manner of application, blights (diseases) and pests to be applied, cultivated crops to be protected, animals to be applied and the like.

In the following, there are shown formulation examples of compositions for controlling and/or preventing pests and blights (diseases), said compositions containing the compounds of the present invention as an active ingredient. These examples are merely illustrative and not to restrict the present invention. Incidentally, in the following examples, "part" means "part by weight".

| Formulation Example 1 | Emulsifiable concentrates |
|---|---|
| Compound No. 156 | 20 parts |
| Xylene | 50 parts |
| N,N—dimethylformamide | 20 parts |
| Solpol 2680 (trade name, a mixture of a non-ionic surfactant and an anionic surfactant supplied by Toho Chemical Industries Co., Ltd., Japan) | 10 parts |

The above components are mixed intimately together to form an emulsifiable concentrate. Upon use, the emulsifiable concentrate is diluted with water up to one fifth to one two thousandth in concentration and applied at a rate of 0.005 to 5 Kg of the active ingredient per hectare.

| Formulation Example 2: | Wettable powders |
|---|---|
| Compound No. 118 | 25 parts |
| Zeeklite PFP (trade name, kaolinite clay supplied by Zeeklite Industries Co., Ltd.) | 67 parts |
| Solpol 5039 (trade name, a mixture of a non-ionic surfactant and an anionic surfactant supplied by Toho Chemical Industries Co., Ltd., Japan) | 5 parts |
| Carplex (anticoagulant) (trade name, a mixture of a surfactant and white carbon supplied by Shionogi Seiyaku K.K., Japan) | 3 parts |

The above components are homogenously mixed together and ground to form a wettable powder. Upon use, the wettable powder is diluted with water up to one five hundredth to one twenty thousandth and applied at a rate of 0.005 to 5 Kg of the active ingredient per hectare.

| Formulation Example 3: | Oil solutions |
|---|---|
| Compound No. 141 | 20 parts |

-continued

| Formulation Example 3: | Oil solutions |
|---|---|
| Methylcellosolve | 80 parts |

The above components are homogeneously mixed together to form an oil solution. Upon use, the oil solution is applied at a rate of 0.005 to 5 Kg of the active ingredient per hectare.

| Formulation Example 4: | Dusts |
|---|---|
| Compound No. 145 | 3.0 parts |
| Carplex (anticoagulant) (trade name, a mixture of a surfactant and white carbon supplied by Shionogi K.K., Japan) | 0.5 part |
| Clay | 95 parts |
| di-isopropyl phosphate | 1.5 parts |

The above components are homogeneously mixed together and ground to form a dust. Upon use, the dust is applied at a rate of 0.005 to 5 Kg of the active ingredient per hectare.

| Formulation Example 5: | Granules |
|---|---|
| Compound No. 147 | 5 parts |
| Bentonite | 54 parts |
| Talc | 40 parts |
| Calcium lignin sulfonate | 1 part |

The above components are mixed intimately together and ground, incorporated with a small amount of water and mixed together under stirring. The resulting mixture is granulated by means of extrusion-granulator and dried to form granules. Upon use, the granule is applied at a rate of 0.005 to 5 Kg of the active ingredient per hectare.

| Formulation Example 6: | Flowable |
|---|---|
| Compound No. 138 | 25 parts |
| Solpol 3353 (trade name, a non-ionic surfactant supplied by Toho Chemical Industries Co., Ltd., Japan) | 10 parts |
| Runox 1000C (trade name, an anionic surfactant supplied by Toho Chemical Industries, Ltd., Japan) | 0.5 part |
| 1% aqueous solution of Xanthan gum (natural high-molecular compound) | 20 parts |
| Water | 44.5 parts |

The above components except the active ingredient are homogeneously mixed together to form a solution, and thereto is added Compound No. 138. The resulting mixture is throughly stirred, wet-ground by means of sand mill to form a flowable. Upon use, the flowable is diluted to one fifth to one two thousandth with water and applied at a rate of 0.005 to 10 Kg of the active ingredient per hectare.

The compounds according to the present invention not only exhibit superior insecticidal action on Hemipterous insect such as green rice leafhopper (*Nephotettix cincticeps*), Lepidopterous insect such as diamondback moth (*Plutella xylostella*), Coleoptera and sanitary and veterinary insect pests such as Dipterous insect pests (e.g., mosquitoes, flies, sand flies, horseflies), Blattariae insect pests, Pulicidae insect pests, and Ixodidae insect pests, but are also useful for expelling mites parasitic on fruits and vegetables such as two-spotted spider mite (*Tetranychus urticae*), Kanzawa spider mite (*Tetranychus kanzawai*), carmine mite (*Tetranychus cinnabarinus*), citrus red mite (*Panonychus citri*) and European red mite (*Panonychus ulmi*); ticks parasitic on animals such as southern cattle tick (*Boophilus microplus*), cattle tick (*Boophilus annulatus*), galf coast tick (*Amblyomma maculatum*), brown-ear tick (*Rhipicephalus appendiculatus*) and *Haemaphysalis longicornis*; as well as flies parasitic on animals such as Dipterous insect pests (e.g., *Lucilia sericata*). Moreover, the compounds of the present invention are also useful for controlling various nematoda parasitic on fruits and vegetables such as root knot nematode, root lesion nematode, cist nematode, etc. The main features of the compounds according to the present invention resides in that the compounds are useful for the prevention or control of blight (or disease) of fruits and vegetables such as powdery mildew, downy mildew, etc. in addition to having the above mentioned insecticidal, acaricidal and nematicidal actions. Moreover, they are excellent as an expellent for ticks and flies parasitic on animals such as domestic animals (e.g., cattle, horse, sheep and pig), domestic fowls, and other animals such as dog, cat, rabbit and the like.

The present invention is explained in detail by way of the following test examples.

TEST EXAMPLE 1

Insecticidal Test on Green Rice Leafhopper (*Nephotettix cincticeps*)

An emulsifiable concentrate containing each of the present compounds was diluted with water to give a 1000 ppm aqueous solution. Stems and leaves by rice-plant were immersed in this solution for 10 seconds and then placed in a glass cylinder. Ten second instar green rice leafhopper larvae which are resistant to organic phosphorous insecticides were released in the cylinder. Then the cylinder was covered with a plastic cap provided with pores and placed in a thermostatic chamber kept at 25° C. Mortality of the larvae after 96 hours was calculated according to the following equation. Incidentally, the test was repeated twice for each compound.

$$\text{Mortality (\%)} = \frac{\text{number of the larvae killed}}{\text{number of the larvae released}} \times 100$$

As the results, the following compounds showed a mortality of 100%.

Compound Nos.: 74, 85, 116, 117, 119, 123, 125, 128, 140, 141, 142, 144, 145, 146, 147, 152, 155, 156, 157, 162, 194, 195, 197, 218, 219, 220, 135, 139, 148, 149, 150, 154, 308, 249, 250.

TEST EXAMPLE 2

Contact Insecticidal Test on 28-Spotted Lady Beetle (*Henosepilachna viginitioctopunctata*)

Leaves of tomato were immersed for 10 seconds in a 1000 ppm aqueous solution of a compound of the present invention which had been prepared by diluting with water an emulsifiable concentrate of the compound, and then air-dried. The leaves thus treated were placed in a laboratory dish, into which 10 second instar 28-spotted lady beetle larvae were released. The dish was covered with a cap provided with pores and then placed in a thermostatic chamber kept at 25° C. Mortality of the larvae after 96 hours was calculated according to the equation described in Test Example 1. Incidentally, the test was repeated twice for each compound.

As the results, the following compounds showed a mortality of 100%.

Compound Nos.: 54, 57, 68, 73, 75, 123, 128, 131, 132, 141, 144, 145, 146, 147, 155, 156, 157, 160, 161, 162, 301, 194, 195, 197, 218, 219, 220, 221, 135, 136, 139, 148, 149, 150, 154, 159, 308, 309, 249, 250, 254.

TEST EXAMPLE 3

Acaricidal Test on Kanzawa Spider Mite (*T. Kanzawai*)

A leaf of kideny bean was cut into a round piece of 1.5 cm in diameter by a leaf punch, and then placed on a moistened filter paper on a styrol cup of 7 cm in diameter. Each piece of the leaf was inoculated with 10 Kanzawa spider mite nymphs. Half a day after the inoculation, to each styrol cup was applied 2 ml of an aqueous solution containing 1000 ppm of a compound of the present invention which had been prepared by diluting an emulsifiable concentrate of the compound with water containing an extender by means of a rotary spray tower. After 96 hours, mortality of the nymph was calculated according to the equation described in Test Example 1. Incidentally, the test was repeated twice for each compound.

As the results, the following compounds showed a mortality of 100%.

Compound Nos.: 2, 11, 28, 55, 68, 72, 73, 74, 75, 113, 116, 118, 119, 122, 123, 125, 128, 138, 140, 141, 142, 144, 145, 146, 147, 155, 156, 157, 194, 195, 196, 197, 218, 219, 220, 221, 135, 136, 139, 149, 150, 154, 159, 307, 308, 240, 241, 242, 256.

Test Example 4

Test for Controlling Downy Mildew of Cucumber

To cucumbers (variety: Sagamihanjiro) which had been grown in pots for 2 weeks was sprayed at a rate of 20 ml per pot a 500 ppm aqueous solution of a compound of the present invention which had been prepared by diluting with water an emulsifiable concentrate of the compound. Each pot was placed in a green house for one day, and then thereto was sprayed a suspension of spores of *Pseudoperonospora cubensis* (the concentration of the suspension being such that 15 spores can be observed by a 150 magnification microscope) to inoculate the cucumber with the spores. The cucumbers inoculated therewith were placed in a room at 25° C. with a relative humidity of 100% for 24 hours and then in a green house for observation of disease appearance.

As the results, no disease appearance was observed at all when the following compounds were used.

Compound Nos.: 53, 54, 55, 57, 68, 75, 128, 131, 132, 141, 144, 145, 156, 160, 161, 301, 149, 154, 238, 242, 255.

TEST EXAMPLE 5

Test for Controlling Powdery Mildew of Cucumber

To cucumbers (variety: Sagamihanjiro) which had been grown in pots for 2 weeks was sprayed, at a rate of 20 ml per pot, a 1000 ppm solution of a compound of the present invention which had been prepared by diluting an emulsifiable concentrate of the compound with water. After each pot was placed for one day in a green house, a suspension of spores of *Sphaerotheca fuliginea* (the concentration of the spore being such that 25 spores can be observed by a 150 magnification microscope) was sprayed to the cucumbers for inoculation. The cucumbers thus treated were placed in a green house at 25°-30° C. for observation of disease appearance. Ten days after the inoculation, percentage of the disease appearance was evaluated. As the results, no disease appearance was observed at all when the following compounds were used.

Compound Nos.: 135, 150, 238.

What is claimed is:

1. A 4(3H)-pyrimidinone compound having the following formula:

$$R^1-N \overset{O}{\underset{\underset{R^2}{\parallel}}{\overset{\parallel}{C}}} \overset{X}{\underset{N}{\overset{}{\bigg|}}} Y-A-Q$$

wherein $R^1$ represents an alkyl group having 1 to 10 carbon atoms, an alkenyl group having 2 to 5 carbon atoms or a cycloalkyl group having 3 to 8 carbon atoms;

$R^2$ represents hydrogen atom, an alkyl group having 1 to 5 carbon atom, an alkoxy group having 1 to 5 carbon atoms, an alkylthio group having 1 to 5 carbon atoms or a phenyl group, and, $R^1$ and $R^2$ together form a member of $$\overset{CH_2-}{\underset{CH_2}{\diagup}} \\ \overset{}{\diagdown} S-$$

X represents halogen atom, an alkyl group having 1 to 5 carbon atoms, a phenyl group, a benzyl group, or an alkoy group having 1 to 5 carbon atoms;

Y represents an oxygen atom or sulfur atom;

A represents $$-\overset{R^3}{\underset{}{\overset{|}{C}H}}-, \quad -CH_2-\overset{R^5}{\underset{}{\overset{|}{C}}}=CH-$$

or $-CH_2-CH_2-O-$, $R^3$ and $R^5$ represent hydrogen atom or an alkyl group having 1 to 5 carbon atoms;

Q represents a phenyl group having substituents or pyridine which may have substituents wherein substituents for Q are selected from the group consisting of halogen atom, an alkyl group having 1 to 10 carbon atoms, a cycloalkyl group having 3 to 6 carbon atoms, an alkyloxy group having 1 to 10 carbon atoms, a haloalkyl group having 1 to 5 carbon atoms, an alkoxyalkyl group having 2 to 5 carbon atoms, a cyanoalkyl group having 2 to 5 carbon atoms, $$\text{phenyl-}W_m, \quad -O-\text{phenyl-}W_m$$

-continued

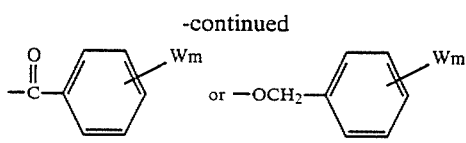

wherein W represents halogen atom, an alkyl group having 1 to 5 carbon atoms, an alkoxy group having 1 to 5 carbon atoms or a haloalkyl group having 1 to 5 carbon atoms, and m represents zero or an integer of from 1 to 4, said W being the same or different when m is an integer of 2 to 4, the number of said substituents being from 1 to 4 and said substituents being the same or different when the number thereof is 2, 3 or 4.

2. A 4(3H)-pyrimidinone compound having the following formula:

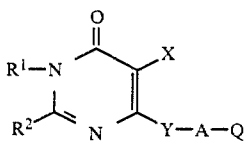

wherein $R^1$ represents an alkyl group having 1 to 10 carbon atoms; $R^2$ represents an alkyl group having 1 to 5 carbon atoms or an alkylthio group having 1 to 5 carbon atoms; X represents a halogen atom or an alkyl group having 1 to 5 carbon atoms; Y represents oxygen atom or sulfur atom; A represents —$CH_2$—, Q represents

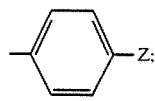

Z represents an alkyl group having 1 to 10 carbon atoms, a cycloalkyl group having 3 to 6 carbon atoms, an alkoxy group having 1 to 10 carbon atoms,

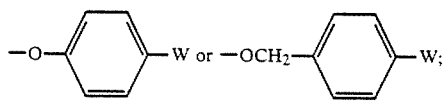

W represents hydrogen atom, halogen atom, an alkyl group having 1 to 5 carbon atoms or a haloalkyl group having 1 to 5 carbon atoms.

3. The compound of claim 1, wherein the compound has the following formula:

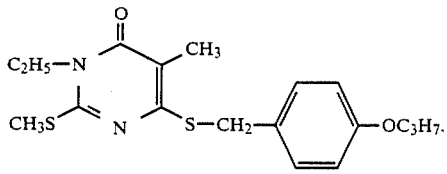

4. The compound of claim 1, wherein the compound has the followng formula:

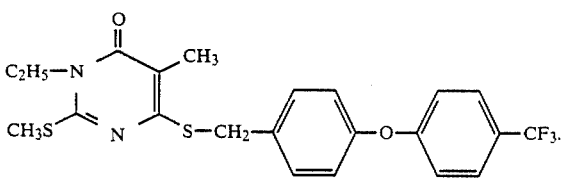

5. The compound of claim 1, wherein the compound has the following formula:

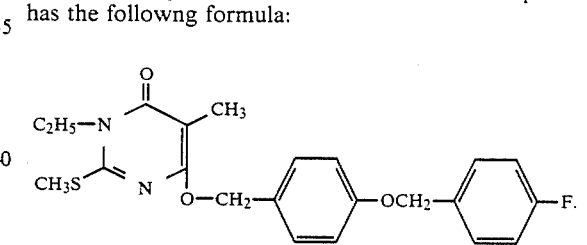

6. The compound of claim 1, wherein the followng formula:

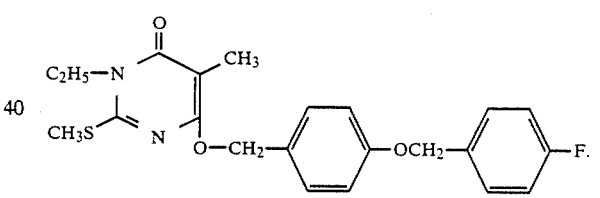

7. A composition suitable for agricultural and horticultural uses comprising at least one 4(3H)-pyrimidone compound of claim 1 and an agriculturally acceptable carrier, said 4(3H)-pyrimidone compound being present in an amount effective to control insects, acarids, nematodes or fungi.

* * * * *